United States Patent
Shelley et al.

(10) Patent No.: US 7,115,869 B2
(45) Date of Patent: Oct. 3, 2006

(54) METHOD FOR MEASUREMENT OF COMPOSITE HEAT DAMAGE WITH INFRARED SPECTROSCOPY

(75) Inventors: Paul H. Shelley, Lakewood, WA (US); Jeffrey R. Kollgaard, Kent, WA (US); Diane R. LaRiviere, Seattle, WA (US)

(73) Assignee: The Boeing Company, Chicago, IL (US)

( * ) Notice: Subject to any disclaimer, the term of this patent is extended or adjusted under 35 U.S.C. 154(b) by 246 days.

(21) Appl. No.: 10/676,302

(22) Filed: Sep. 30, 2003

(65) Prior Publication Data

US 2005/0067569 A1 Mar. 31, 2005

(51) Int. Cl.
*G01N 21/00* (2006.01)

(52) U.S. Cl. .................................................. 250/341.8
(58) Field of Classification Search ............... 250/341.8
See application file for complete search history.

(56) References Cited

U.S. PATENT DOCUMENTS

| | | | |
|---|---|---|---|
| 3,017,512 A | | 1/1962 | Wolbert et al. |
| 3,733,485 A | * | 5/1973 | Gaynor et al. ............. 250/331 |
| 3,994,586 A | | 11/1976 | Sharkins et al. |
| 4,703,187 A | | 10/1987 | Hofling et al. |
| 4,748,329 A | | 5/1988 | Cielo et al. |
| 4,800,279 A | | 1/1989 | Hieftje et al. |
| 5,091,647 A | | 2/1992 | Carduner et al. |
| 5,289,266 A | | 2/1994 | Shih et al. |
| 5,483,338 A | | 1/1996 | Wachter et al. |
| 5,573,952 A | | 11/1996 | Moessner |
| 6,184,528 B1 | | 2/2001 | DiMarzio et al. |
| 6,671,047 B1 | * | 12/2003 | Opsal et al. ................ 356/369 |
| 6,675,029 B1 | | 1/2004 | Monfre et al. |
| 6,697,654 B1 | | 2/2004 | Lorenz et al. |
| 6,734,962 B1 | | 5/2004 | Treado et al. |
| 6,794,651 B1 | | 9/2004 | Shelley et al. |
| 6,853,926 B1 | | 2/2005 | Alfano et al. |
| 6,895,360 B1 | | 5/2005 | Liu et al. |
| 6,919,957 B1 | * | 7/2005 | Nikoonahad et al. .... 356/237.2 |

FOREIGN PATENT DOCUMENTS

| | | |
|---|---|---|
| FR | 2680240 | 2/1993 |
| WO | WO 2004/048888 | 6/2004 |

OTHER PUBLICATIONS

Standard Guide for Preparation of Aluminum Surfaces for Structural Adhesives Bonding (Phosphoric Acid Anodizing), ASTM International Designation: D 3933-98, Copyright 2003, pp. 3-4, American Society for Testing and Materials, 100 Barr Harbor Dr., West Conshohocken, PA 19428.

(Continued)

*Primary Examiner*—Otilia Gabor
(74) *Attorney, Agent, or Firm*—Lee & Hayes PLLC

(57) ABSTRACT

A non-destructive method determines an amount of heat exposure to a resin-fiber composite substrate. A value of infrared energy reflected by a composite substrate is determined. The value of infrared energy reflected, or conversely absorbed, is correlated to a degree or amount of heat exposure. According to an aspect of the present invention, one method utilizes an infrared spectrometer to determine infrared absorbance of a composite substrate. The infrared energy of the reflected beam is then compared with the pre-determined value of infrared energy reflected off a reference heat damaged composite substrate to determine the amount of heat exposure.

55 Claims, 20 Drawing Sheets

OTHER PUBLICATIONS

Palovic, et al., "Optical and Microstructural Properties of Anodically Oxidized Aluminum", Elsevier Sequoia, Thin Solid Films 138, pp. 97-109, 1986.

Laet, et al., "Development of an Optical Model for Steady State Porous Anodic Films on Aluminum Formed in Phosphoric Acid", Elsevier, This Solid Films, 320, pp. 241-252, 1998.

Anicai, "Analysis of Electrochemical Colored Aluminum Anodic Films in AgNO3-Based Electrolytes by Diffuse Reflectance Spectra", Elsevier Science, Inc., Metal Finishing, pp. 10-13, 1998.

G.L. Powell et al., "Nondestructive Inspection of Graphite-Epoxy Laminates for Heat Damage Using Drift and LPF Spectroscopies," Proc. of a Conference on Characterization and NDE of Heat Damage in Graphite Epoxy Composites, NTIAC, in print (1993).

Mehrkam, et al., "Detection of Composite Heat Damage by Drift Spectroscopy", 38th International SAMPLE Symposium, pp. 217-223, May 10-13, 1993.

Drukker, et al., "Mechanical and Chemical Consequences of Through Thickness Thermal Gradients in Polyimide Matric Composite Materials", Composites Part A: Applied Science and Manufacturing 34, pp. 125-133, 2003.

* cited by examiner

METHOD FOR MEASUREMENT OF COMPOSITE HEAT DAMAGE WITH INFRARED SPECTROSCOPY

FIELD OF THE INVENTION

This invention relates generally to measurement, and, more specifically, to measurement of heat damage to materials.

BACKGROUND OF THE INVENTION

Resin-fiber composites are utilized in a variety of applications, such as parts of vehicles, including aircraft. Vehicles, equipment, and structures constructed utilizing resin-fiber composites may be exposed to heat in a variety of circumstances, ranging from fire to lightening strikes to weapons impacts.

Heat exposure to resin-fiber composite affects the composites in a variety of ways. Chemical degradation may occur involving changes in the polymer chemical structure. This may include oxidation, material loss and either the breaking or forming of additional chemical links. Resin decomposition, charring, and ultimately fiber decomposition may occur at increasing temperatures. Repair or removal of heat damaged resin-fiber composite materials involves determining the degree of harmful heat damage to the composite substrate. Ascertaining the degree of heat damage to composite materials is typically performed by visual inspection, but heat damage to resin-fiber composites is not always visually apparent. Thus, current visual heat damage inspections of resin-fiber composites involve a substantial degree of subjectivity. Therefore, there currently exists an unmet need in the art for a non-destructive, quantitative, objective determination of a degree of heat damage to resin-fiber composite materials.

SUMMARY OF THE INVENTION

The present invention provides a non-destructive method for efficiently and objectively determining the degree of heat exposure to a resin-fiber composite material. The present invention may be utilized to quantitatively determine the degree of heat exposure of a composite.

According to one embodiment of the invention, a value of infrared energy reflected by a surface on a composite substrate is determined. The value of infrared energy reflected, or conversely absorbed, is correlated to a degree or amount of heat exposure.

According to one aspect of the present invention, an infrared spectrometer is utilized to determine infrared absorbance at appropriate wavelengths of a composite substrate. The infrared energy of the reflected beam is then compared with the pre-determined value of infrared energy reflected off a reference heat-damaged composite substrate to determine the amount of heat exposure.

According to another aspect of the present invention, a difference between infrared energy absorbance of a heat damaged composite substrate at two wavelengths is compared with a reference surface.

BRIEF DESCRIPTION OF THE DRAWINGS

The preferred and alternative embodiments of the present invention are described in detail below with reference to the following drawings.

DETAILED DESCRIPTION OF THE INVENTION

By way of overview, a non-destructive method is provided for determining an amount of heat exposure to a resin-fiber composite substrate. A value $I_s$ of infrared energy reflected by a surface on a composite substrate is determined at appropriate wavelengths. The value $I_s$ of infrared energy reflected by the composite substrate correlates to an amount of heat exposure. Within the infrared spectrum, absorbance varies with heat exposure and thus infrared absorbance can be correlated to heat exposure to resin-fiber composites.

Figure 1:
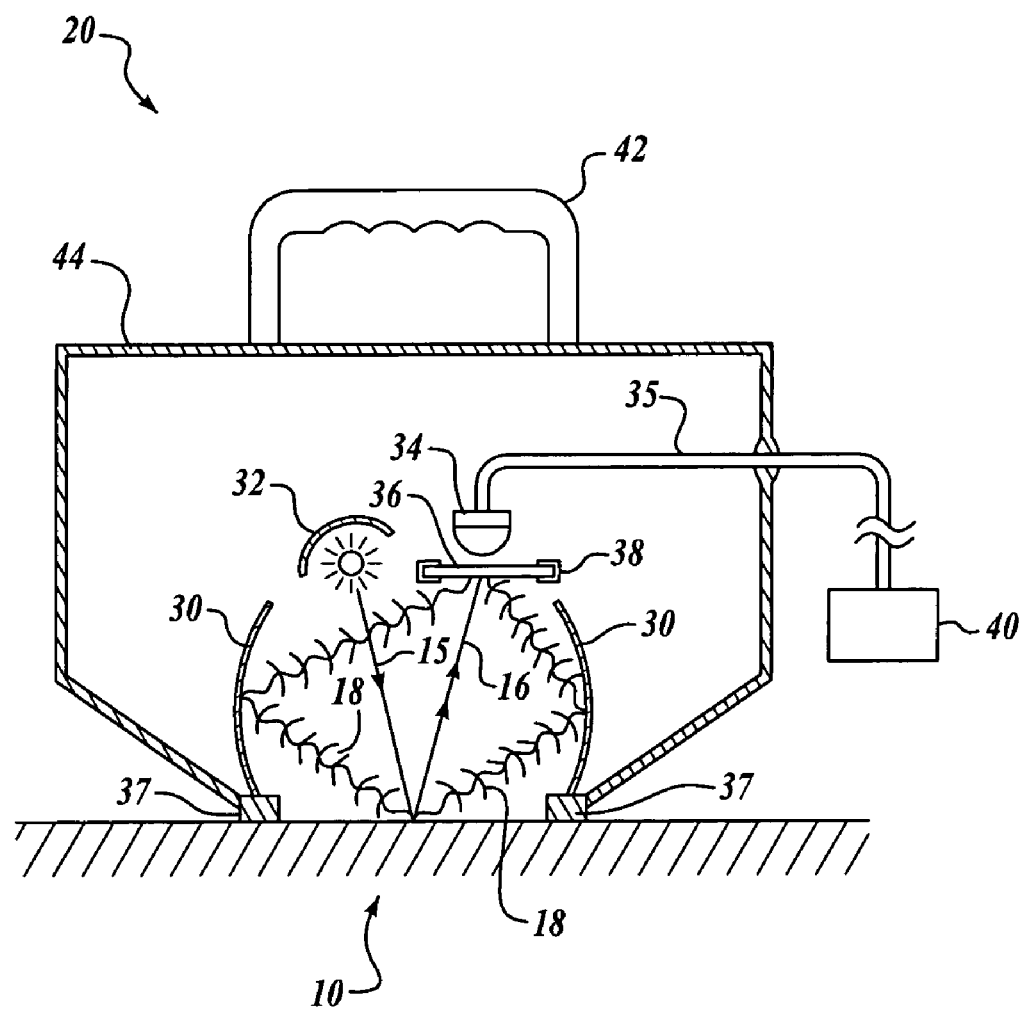
FIG. 1 is a cross section of an exemplary heat damage measurement device in accordance with the present invention.

FIG. 1 is a cross section drawing of an exemplary testing device 20 used to determine the amount of heat exposure to a resin-fiber composite substrate according to a presently preferred embodiment of the invention. An infrared transmission beam 15 is transmitted by an infrared source 32. The beam 15 is reflected off a sample surface 10, and the reflected beam 16 is detected by an infrared detector 34. The infrared source 32 suitably may include a multi-frequency infrared source 32 and the infrared detector 34 may include a single or multi-frequency infrared detector 34. In the embodiment shown in FIG. 1, the infrared detector detects infrared energy passing through a filter 36 removeably held by a filter holder 38. This permits the filter 36 to be switched to allow use of the testing device 20 at different infrared frequencies. The infrared levels received by the infrared detector 34 are output as an electrical signal to a processor display 40 through a conductor 35.

In one presently preferred embodiment, by way of example and not limitation the infrared source 32 and the infrared detector 34 suitably include a hand-held infrared filter spectrometer such as the SOC410, manufactured by Surface Optics Corporation. In alternative embodiments, an infrared Fourier transform imaging spectrometer, or a portable infrared spectrometer may be utilized. In the exemplary testing device 20, the infrared source 32 and infrared detector 34 are suitably enclosed within a housing 44 with feet 37. The feet 37 rest against the substrate 10 when a sample is tested.

The exemplary testing device 20 shown in FIG. 1, by way of example and not limitation, also collects diffuse reflected infrared radiation diffusely reflected by the substrate 10. The diffuse reflected infrared energy 18 is collected by an ellipsoidal mirror 30 and directed towards the infrared detector 34. It will be appreciated that embodiments of the present invention may suitably utilize specular (i.e., direct reflectance), diffuse reflectance, or alternative collectors, such as an attenuated total reflectance collector as described in reference to FIG. 2 below.

The feet 37 of the testing device 20 hold the infrared source 32 and the infrared detector 34 at a predetermined distance and position relative to the surface 10. The mobility of the testing device 20 permits additional measurement of adjoining areas and other samples with comparable results.

The testing device 20 of FIG. 1 may be utilized to non-destructively determine the degree or the amount of heat exposure of the substrate 10. Initially, the infrared absorbance values of heat exposed reference composite samples (not shown) are determined by measuring the $I_r$ of infrared energy reflected from a reference composite surface. Absorbance A is calculated as $-\log 10 \, (I/I_o)$ where $I_o$ is the value of infrared energy reflected by a base material, often gold, and I is the value of infrared energy reflected by the sample under study. The device 20 is then used to transmit the infrared beam 15 to the substrate 10 to be tested, and a value $I_s$ of infrared energy reflected by the substrate 10 is measured. Absorbance is derived as described above and comparison is made between the absorbance of the substrate 10 and the absorbance of the heat exposed reference samples (not shown) to calculate an amount of heat exposure. It will be appreciated that surface coatings, or other contaminants, may affect infrared absorbance of the composite substrate measured. Thus, or surface coatings to the composite are typically removed prior to such infrared measurements. It will also be appreciated $I_s$ may be compared with $I_r$ without calculating absorbance. However calculating and utilizing absorbance provides graphing and calculating convenience.

Figure 2:
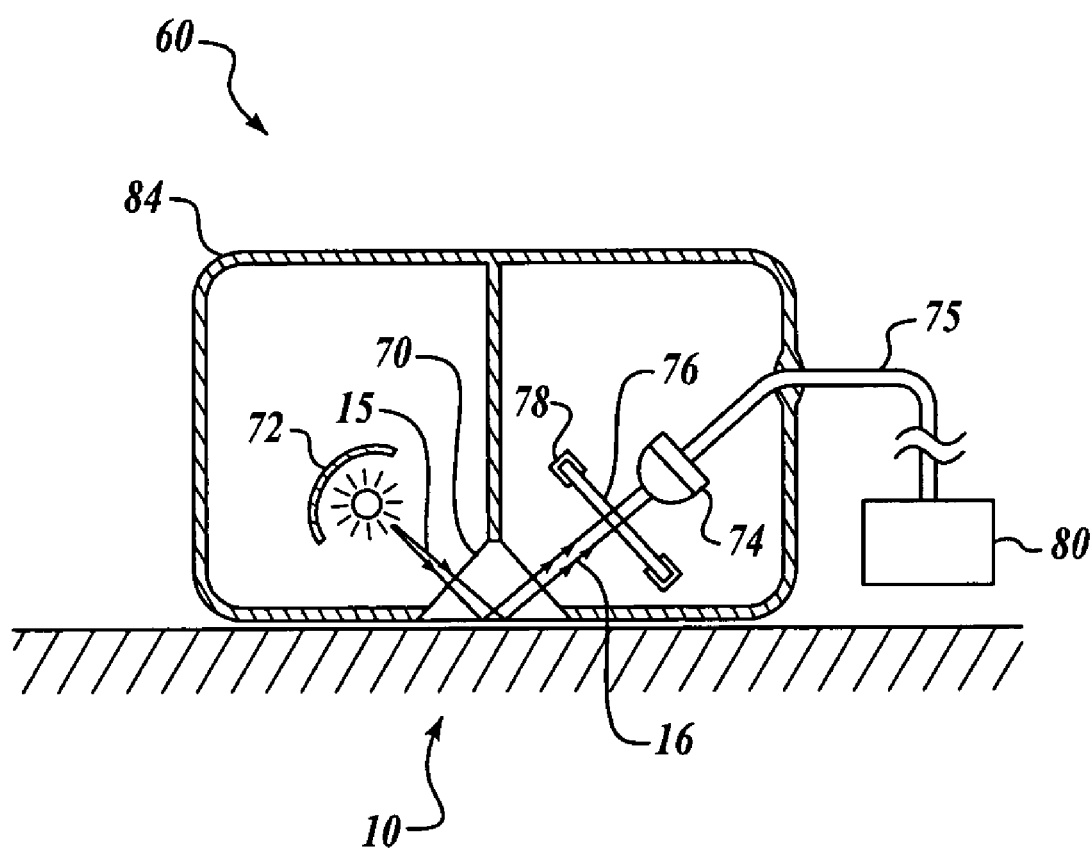
FIG. 2 is a cross section of an exemplary heat damage measurement device utilizing attenuated total reflectance in accordance with the present invention.

FIG. 2 is a cross section of an alternative exemplary testing device 60 that may be utilized to determine the amount of heat damage to a resin-fiber composite substrate 10 according to an alternate embodiment of the invention. An infrared beam 15 is transmitted by an infrared source 32. The beam 15 is transmitted through a crystal 70 placed against the substrate 10. The beam 15 is reflected off the lower surface of the crystal 70, but due to an interaction of the infrared energy with the crystal 70 in contact with the substrate 10, a portion of the infrared energy is absorbed. The reflected attenuated beam 16 is then detected by an infrared detector 74. As is known in the art, the use of a crystal 70 in this manner is referred to as attenuated total reflectance (ATR).

In this exemplary embodiment, the reflected beam 16 passes through a filter 76 removeably held in a filter holder 78. An infrared detector 74 then detects the infrared energy of the reflected beam at the frequency passed by the filter 76. It will be appreciated that a number of suitable filters may be successively placed in the filter holder 78, thereby permitting measurement of the attenuated total reflectance of the substrate 10 at a variety of frequencies. Output from the infrared detector 74 is transmitted through a conductor 75 to a processor 80 for recording or analysis. The infrared source 72, crystal 70, and collector 74 are suitably enclosed in a housing 84. The housing 84 may be successively placed against the substrate 10 thereby permitting measurements to be taken at a variety of locations and surfaces. The device 60 thus may detect attenuated infrared reflectance suitably utilizing one or more narrow pass filters 76, and a broad band infrared source 72. It will be appreciated that in alternative embodiments, by way of example but not limitation, an infrared spectrometer may be incorporated in the device 60 to permit measurement of attenuated total reflectance of the substrate 10 over a continuous frequency range.

Figure 3:
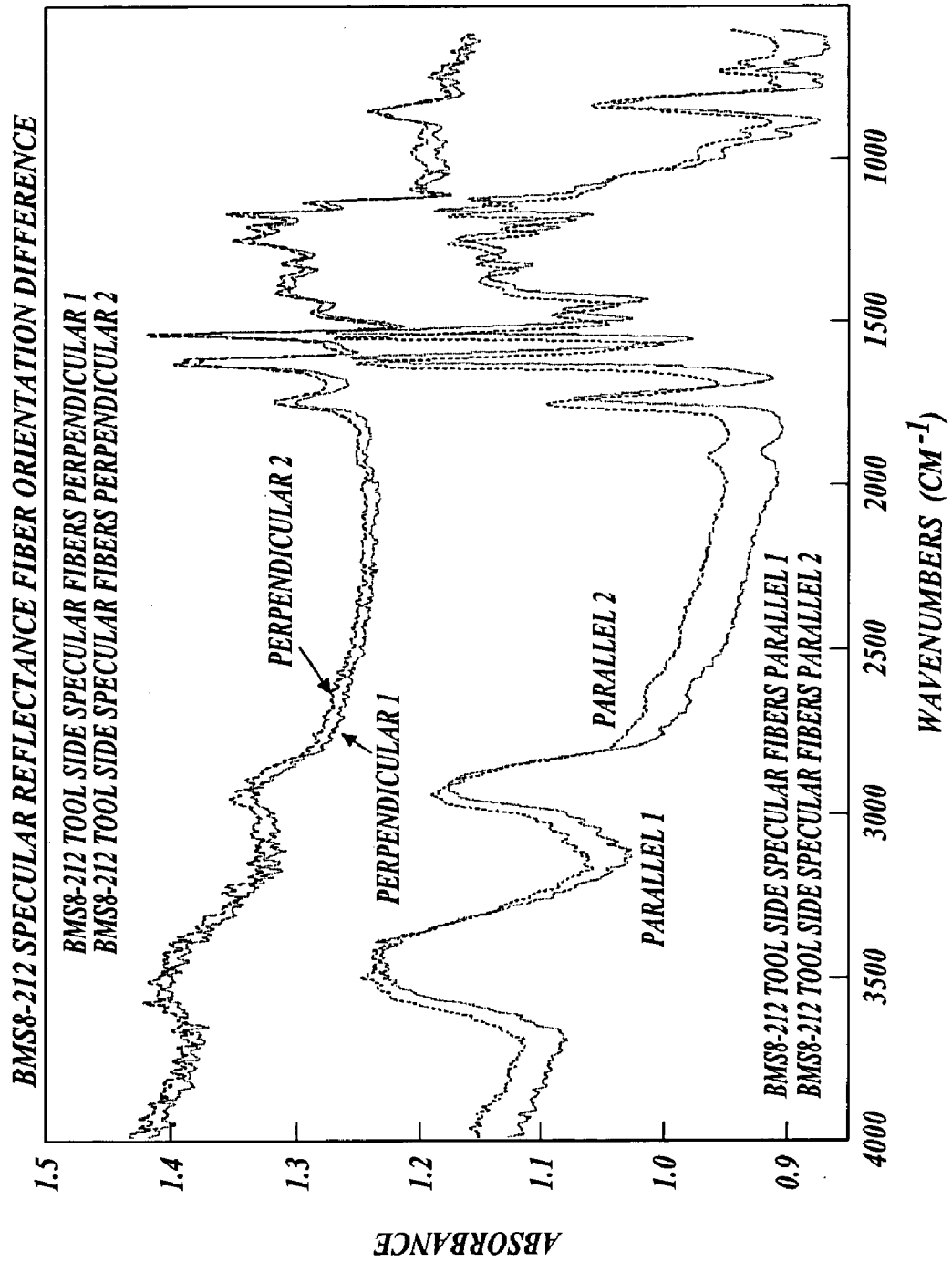
FIG. 3 is a graph of infrared absorbance parallel and perpendicular to fibers in a composite substrate.

Through testing, it has been determined that the reflectance at infrared frequencies by composite substrates may vary depending upon the orientation of the reflected infrared beam with respect to alignment of the reinforcing fibers in the resin-fiber composite being measured. FIG. 3 is a graph of different reflectances resulting from differences in fiber orientation. Four specular infrared spectra are measured over a range of wavenumbers (cm-1), two spectra are measured approximately parallel to fibers in the resin-fiber composite, and two spectra are measured approximately perpendicular to fibers in the resin-fiber composite. Absorbance spectra denoted parallel 1, parallel 2, perpendicular 1, and perpendicular 2 in FIG. 3 show absorbance versus wavenumbers (in cm-1) from approximately 4000 cm-1 to approximately 400 cm-1 of a first exemplary fiber metal composite designated BMS 8-212 (Boeing Materials Services 8-212). Absorbance in this instance is graphed on a range of approximately 0.85 to 1.45.

As shown in FIG. 3, the spectra taken with reflectance generally in alignment with the fibers in the resin-fiber composite (parallel 1 and parallel 2) show more pronounced absorbance peaks than the spectra (perpendicular 1 and perpendicular 2) taken generally oblique or perpendicular to the fiber alignment in the fiber metal composite. Further, the absorbances of the parallel spectra, parallel 1 and parallel 2, are less than that of the perpendicular 1 and perpendicular 2 spectra by an absorbance amount of approximately 0.3. It will be appreciated that at varying angles to the fiber alignment in the fiber metal composite, substantial variability of specular reflectance of infrared energy may be obtained even for the same sample at the same frequency. Thus, in one presently preferred embodiment, reflectance is measured in a direction in alignment with the fibers of the resin-fiber composite. It will be appreciated that when the surface coatings or contamination of a composite surface are removed for infrared measurements, the fibers are typically visible. Thus, in non-destructive testing of the substrate an operator may conveniently align the measurement device (not shown) to permit the reflectance measurement to be made parallel to the fiber alignment, suitably facilitating uniformity in measuring comparable surfaces.

Figure 4:
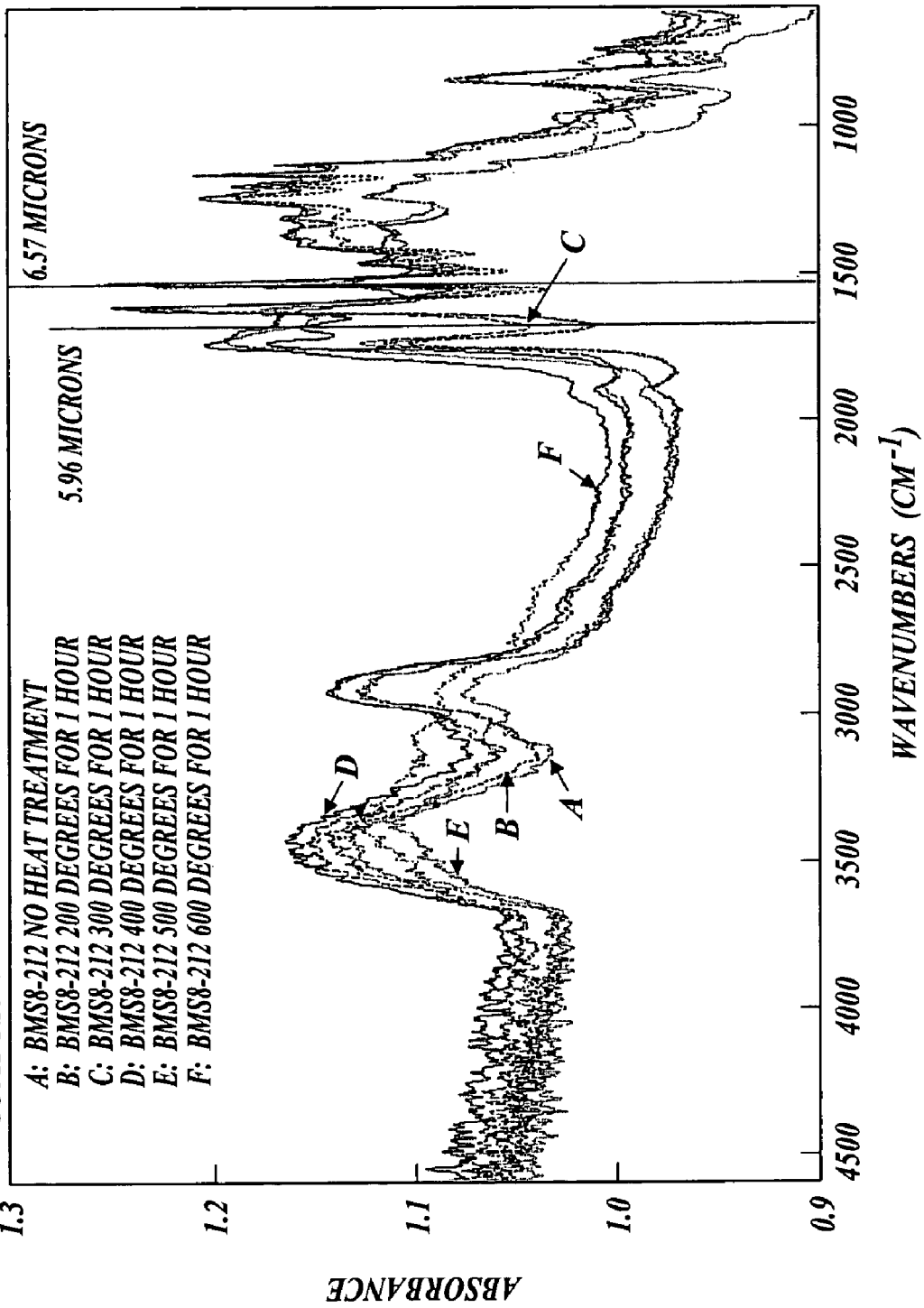
FIG. 4 is a graph of infrared absorbance of a first exemplary resin-fiber composite.

FIG. 4 is a graph of six infrared absorbance specra over a range of wavenumbers from six resin-fiber composite substrates (not shown) exposed to various amounts of heat. Absorbance spectra A–F show absorbance versus wavenumbers from approximately 4600 to approximately 400 cm-1. The resin-fiber substrate tested here includes the first exemplary resin-fiber composite BMS 8-212 with no heat exposure for spectrum A, with 200 degrees heat exposure for 1 hour for spectrum B, 300 degrees for 1 hour for spectrum C, 400 degrees for 1 hour for spectrum D, 500 degrees for 1 hour for spectrum E, and 600 degrees for 1 hour for spectrum F. All of the specra show absorbance peaks near 3500 wavenumbers, 3000 wavenumbers, 1600 wavenumbers, and 1300 wavenumbers. However, variability of the spectra is not always linear, with heat exposure at specific wavenumbers not always directly correlated with heat exposure.

Figure 5:
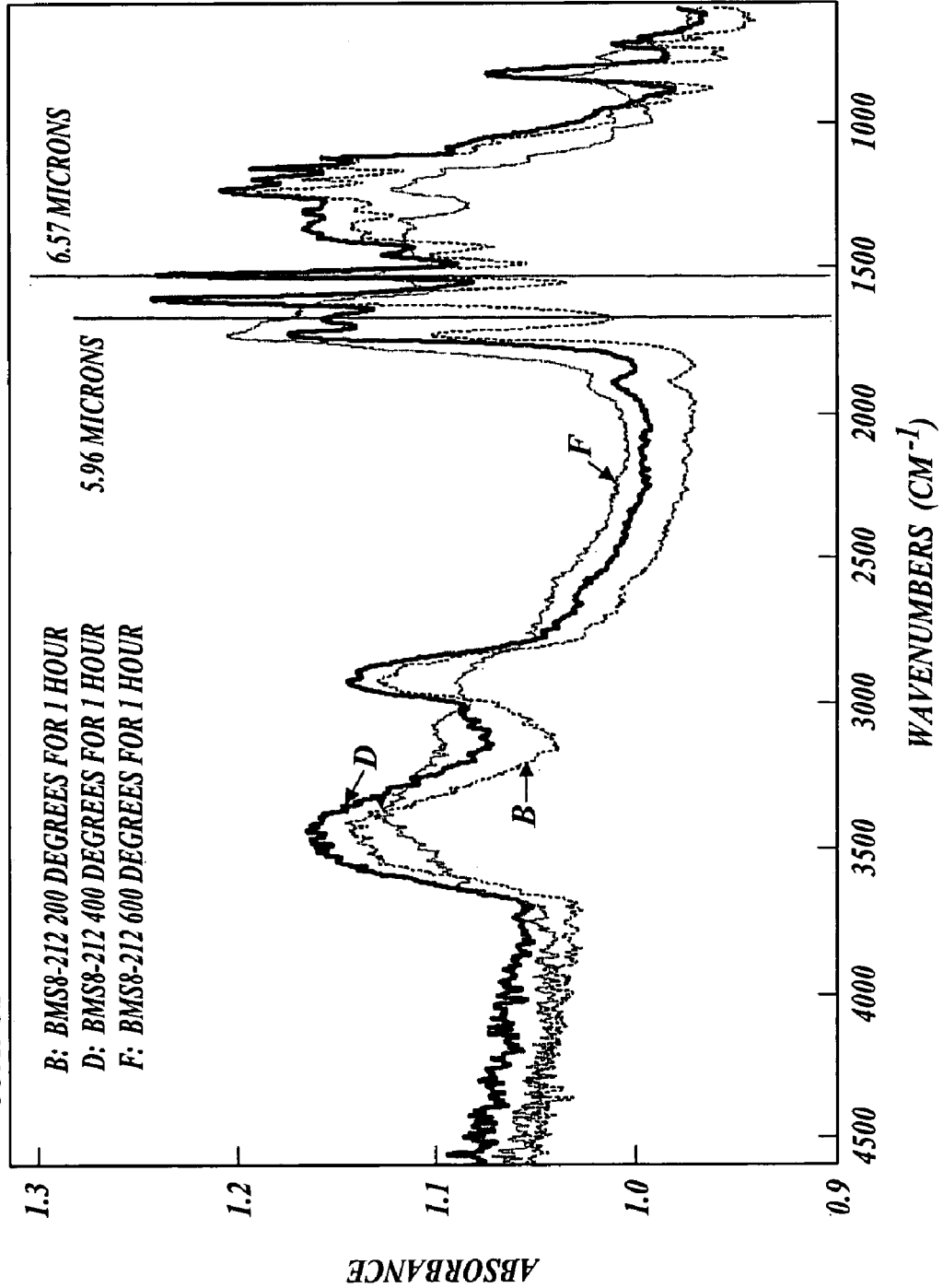
FIG. 5 is a graph of infrared absorbance of a first exemplary resin-fiber composite.

In FIG. 5, three of the spectra of FIG. 4 are shown, and three are deleted, for clarity. Spectrum B shows heat exposure of 200 degrees for 1 hour, spectrum D shows 400 degree exposure for 1 hour, and spectrum F shows 600 degrees exposure for 1 hour for the same first exemplary resin-fiber composite BMS 8-212 over the same range of wavenumbers as FIG. 4. In this example, reference lines at 6.57 µm or 1522 wavenumbers, and 5.96 µm or 1678 wavenumbers are shown. At 5.96 µm absorbance increases with heat exposure while at 6.57 µm absorbance is relatively constant. Similar correlations may be made at different wavenumbers as well, as discussed in connection with FIGS. 6, 7 and 8 below. This permits correlation of infrared absorbance at single and multiple wavenumbers with heat exposure of the resin-fiber composite.

Figure 6:
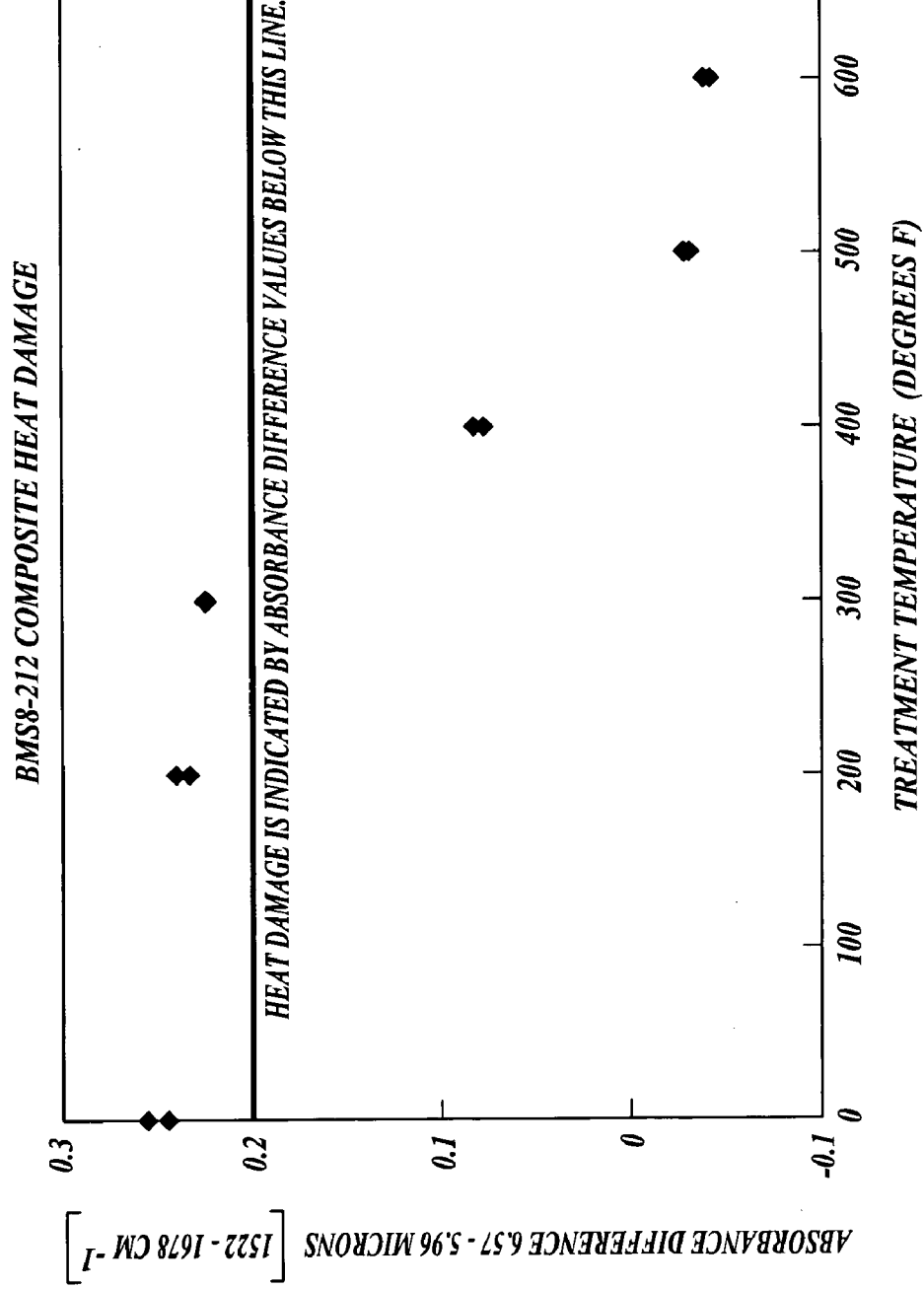
FIG. 6 is a graph of absorbance differences for a first exemplary resin-fiber composite exposed to heat.

Turning to FIG. 6, composite heat damage to the exemplary resin-fiber composite BMS 8-212 may be indicated subtracting absorbances at specified wavenumbers. For example, damage may be indicated ed when absorbance at 1678 cm-1 subtracted from absorbance at 1522 cm-1 equals less than around 0.2, or becomes negative. Temperature exposures of over 300 degrees shows a difference of less than 0.1 and becoming negative as exposure to temperatures increases from 400 to 600 degrees.

FIG. 6 is a plot of this net absorbance difference for 1 hour temperature exposures at the temperatures listed in the following Table A ("ABS"=Absorbance):

TABLE A

| Temperature | ABS @ 6.57 microns − ABS @ 5.96 microns |
|---|---|
| 0 | 0.255 |
| 0 | 0.244 |
| 200 | 0.24 |
| 200 | 0.232 |
| 300 | 0.225 |
| 300 | 0.224 |
| 400 | 0.082 |
| 400 | 0.077 |
| 500 | −0.029 |
| 500 | −0.031 |
| 600 | −0.041 |
| 600 | −0.038 |

Figure 7:
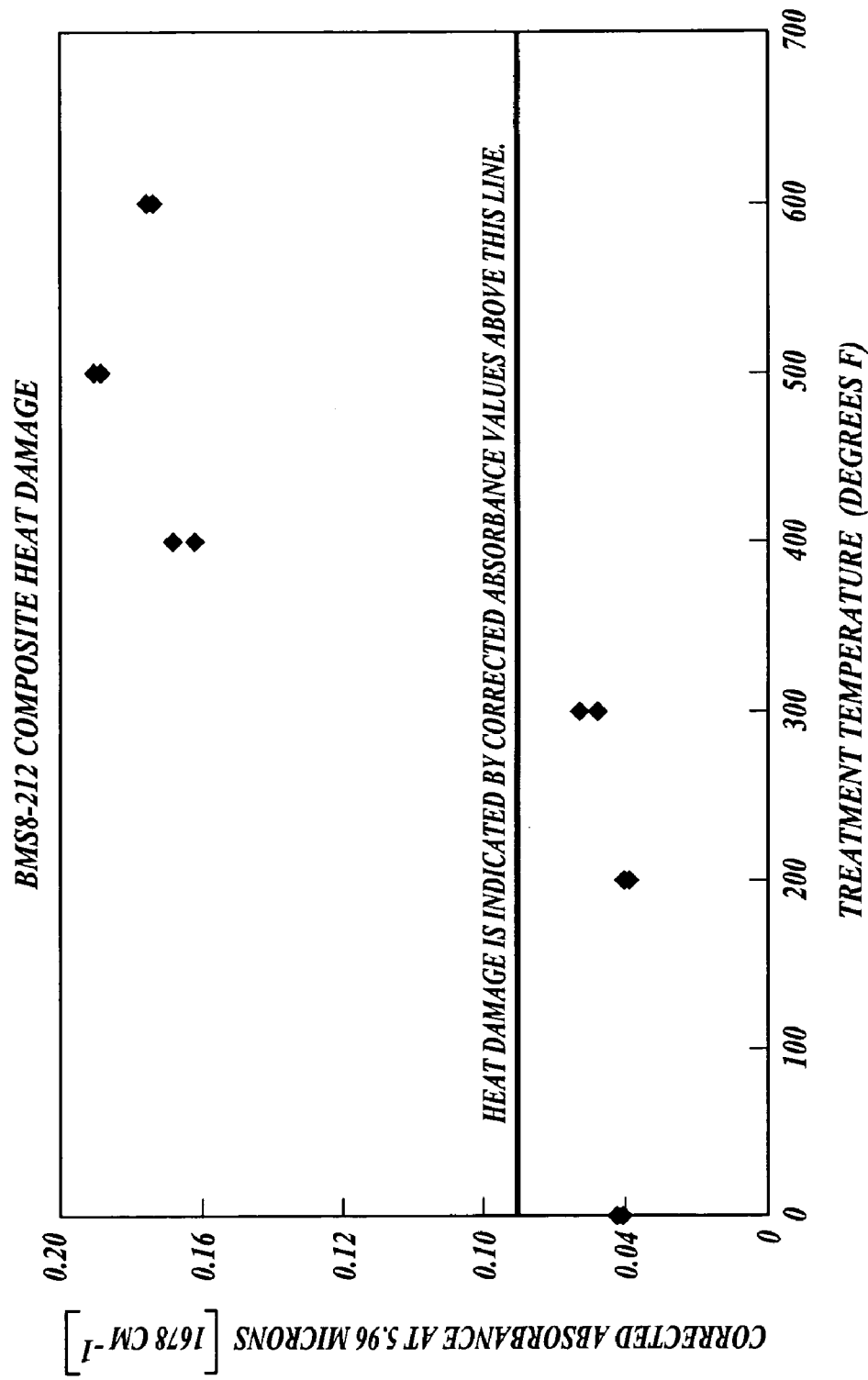
FIG. 7 is a graph of corrected absorbance for a first exemplary resin-fiber composite exposed to heat.

In an alternate embodiment of the present invention, heat damage to the exemplary composite BMS 8-212 may be indicated by corrected absorbance values at 1678 cm-1. The absorbance, by way of example but not limitation, may be corrected by subtracting a reference absorbance at 2000 wavenumbers. In FIG. 7 heat damage of exposure over 1 hour to 400 degrees F. or higher is indicated by corrected absorbance greater than 0.07.

The values graphed in FIG. 7 are listed in Table B below:

TABLE B

| Temperature | Corrected Absorbance at 5.96 microns (subtracted reference ABS at 5.00 microns) |
|---|---|
| 0 | 0.043 |
| 0 | 0.041 |
| 200 | 0.041 |
| 200 | 0.039 |
| 300 | 0.048 |
| 300 | 0.053 |
| 400 | 0.162 |
| 400 | 0.168 |
| 500 | 0.19 |
| 500 | 0.188 |
| 600 | 0.175 |
| 600 | 0.174 |

Figure 8:
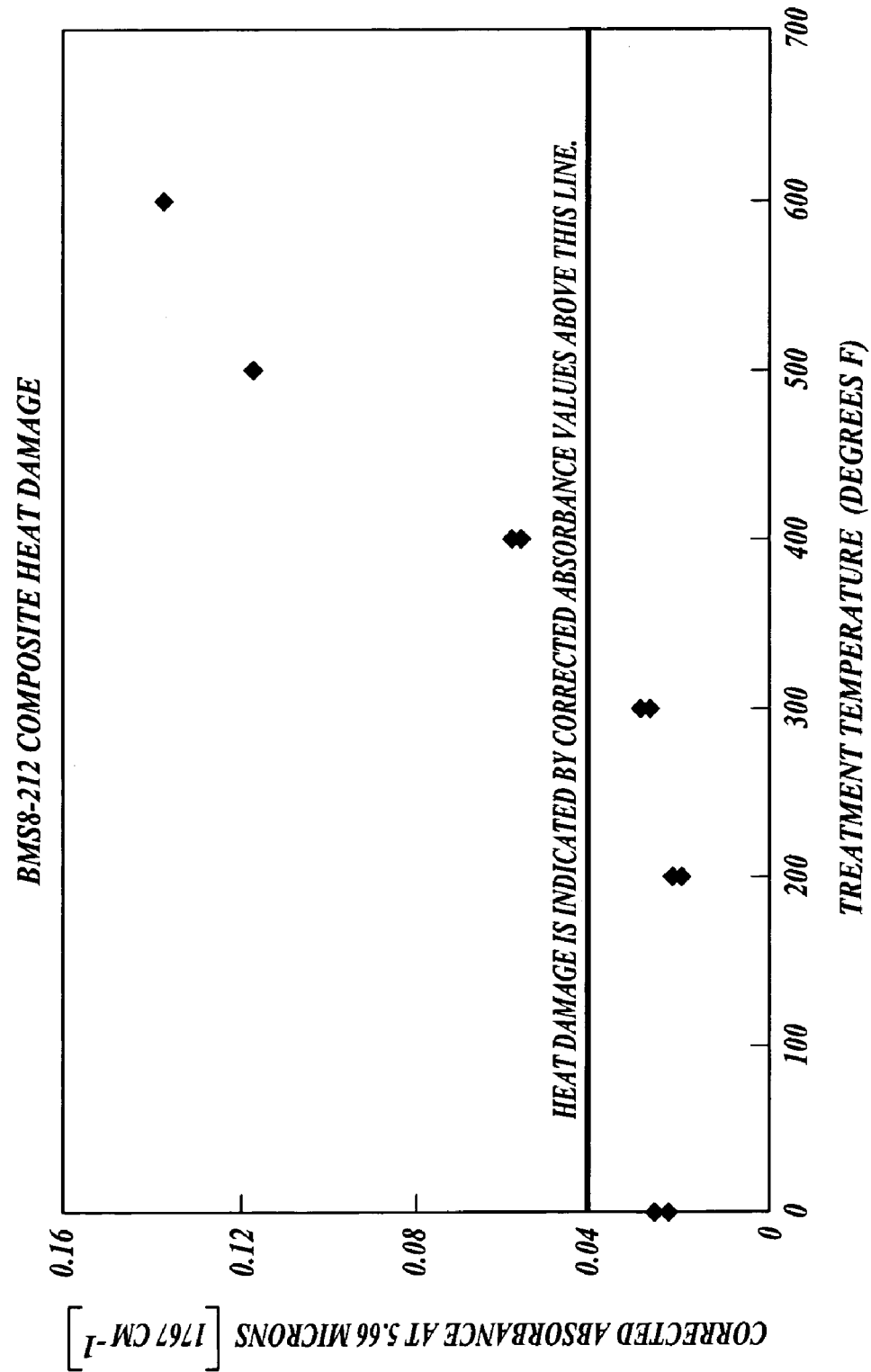
FIG. 8 is a graph of corrected absorbance for a first exemplary resin-fiber composite exposed to heat.

In a further exemplary embodiment as shown in FIG. 8, heat damage may be indicated by absorbance values at around 1767 wavenumbers, or 5.66 µm, for the exemplary resin-fiber composite the BMS 8-212. In this embodiment, the heat damage is indicated by corrected absorbance greater than 0.4 where absorbance at 1767 cm-1 is corrected by subtracting a reference absorbance at 5 µm, or 2000 wavenumbers. Corrected absorbance increases above 0.04 with exposures to greater than 400 degrees Fahrenheit.

FIG. 8 is a graph of the corrected absorbances reflected in Table C as follows:

TABLE C

| Temperature | Corrected Absorbance at 5.66 microns (subtracted reference ABS at 5.00 microns) |
|---|---|
| 0 | 0.026 |
| 0 | 0.023 |
| 200 | 0.02 |
| 200 | 0.022 |
| 300 | 0.027 |
| 300 | 0.029 |
| 400 | 0.056 |
| 400 | 0.058 |
| 500 | 0.117 |
| 500 | 0.117 |
| 600 | 0.137 |
| 600 | 0.137 |

Figure 9:
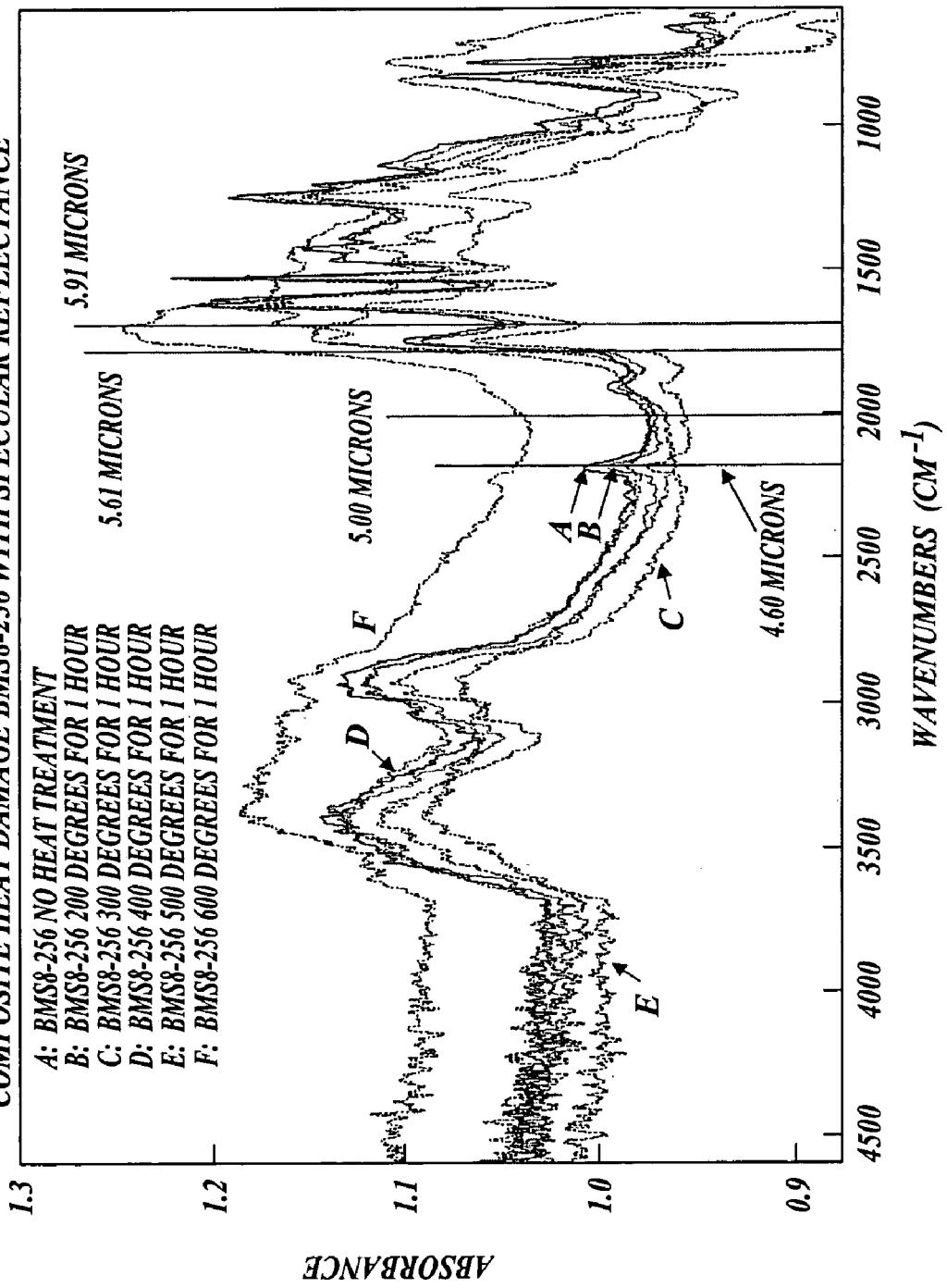
FIG. 9 is a graph of infrared absorbance of a second exemplary resin-fiber composite.

FIG. 9 includes 6 absorbance spectra over a range of wavenumbers from six samples of a second exemplary resin-fiber composite substrate (denoted BMS 8-256) exposed to various amounts of heat. Spectrum A reflects no heat treatment. Spectrum B reflects 200 degrees heat exposure for 1 hour. Spectrum C reflects 300 degrees heat exposure for 1 hour. Spectrum D reflects 400 degree heat exposure for 1 hour. Spectrum E reflects 500 degree exposure for 1 hour. Spectrum F reflects 600 degree heat exposure for 1 hour. Because BMS 8-256 has a different chemical composition than BMS 8-212, its absorbance peaks and responses to heat exposure are somewhat different than that for BMS 8-212 as described in connection with FIGS. 3 and 4 above.

Figure 10:
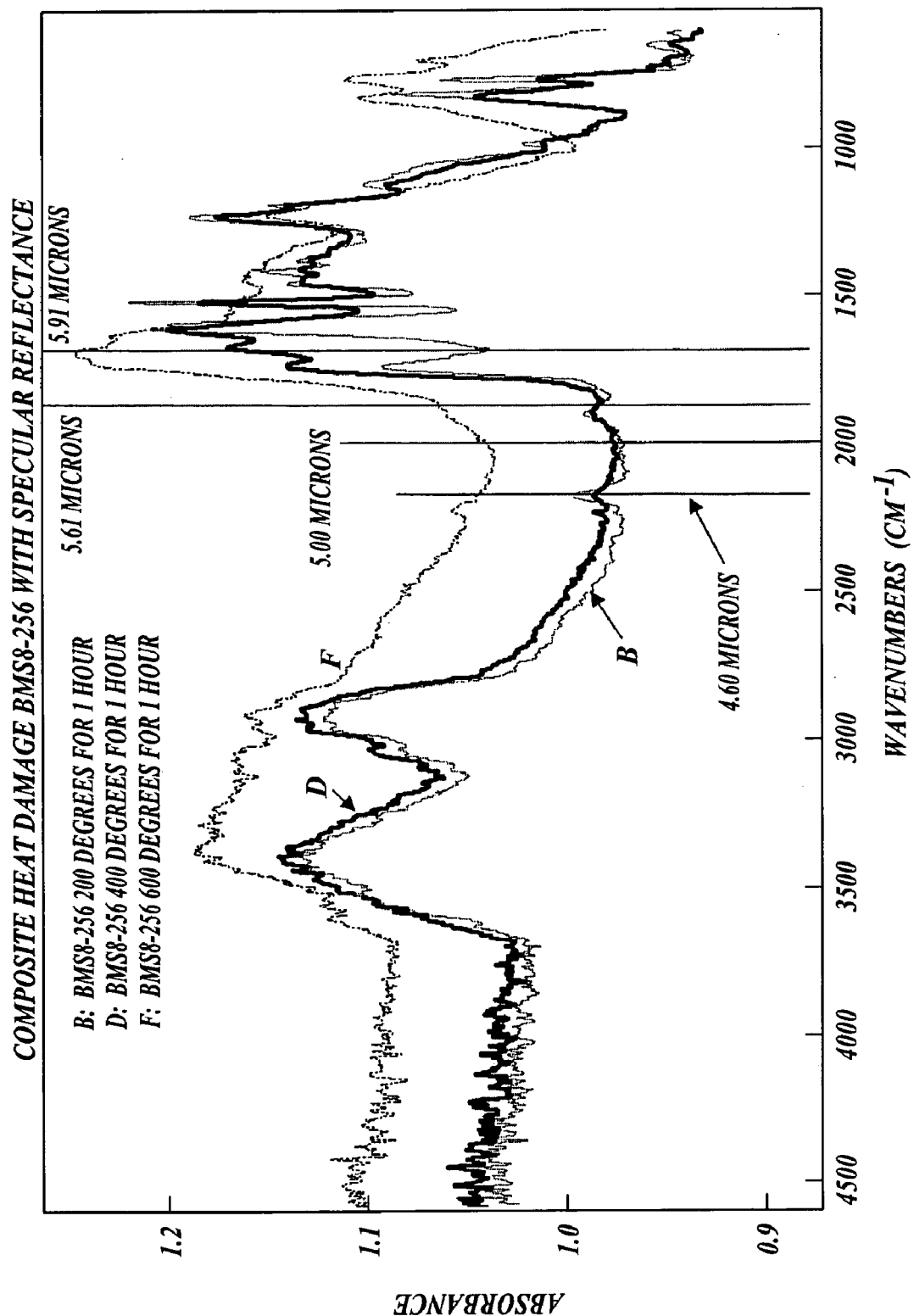
FIG. 10 is a graph of infrared absorbance of a second exemplary resin-fiber composite.

FIG. 10 is a simplified version of FIG. 9 with only spectra B, D and F of FIG. 9 shown. By way of example at approximately 1700 wavenumbers or 5.91 µm, absorbance increases with increasing heat exposure. However, by way of example, at 4.6 µm or 2174 wavenumbers absorbance decreases with increasing heat exposure. This difference is more pronounced when absorbance at a baseline point at 5.00 µm is subtracted from the absorbance at 4.60 µm. See Table E and discussion of FIG. 12, below. The spectra reflected in FIGS. 9 and 10 permit the correlation of heat exposure to absorbance.

Figure 11:
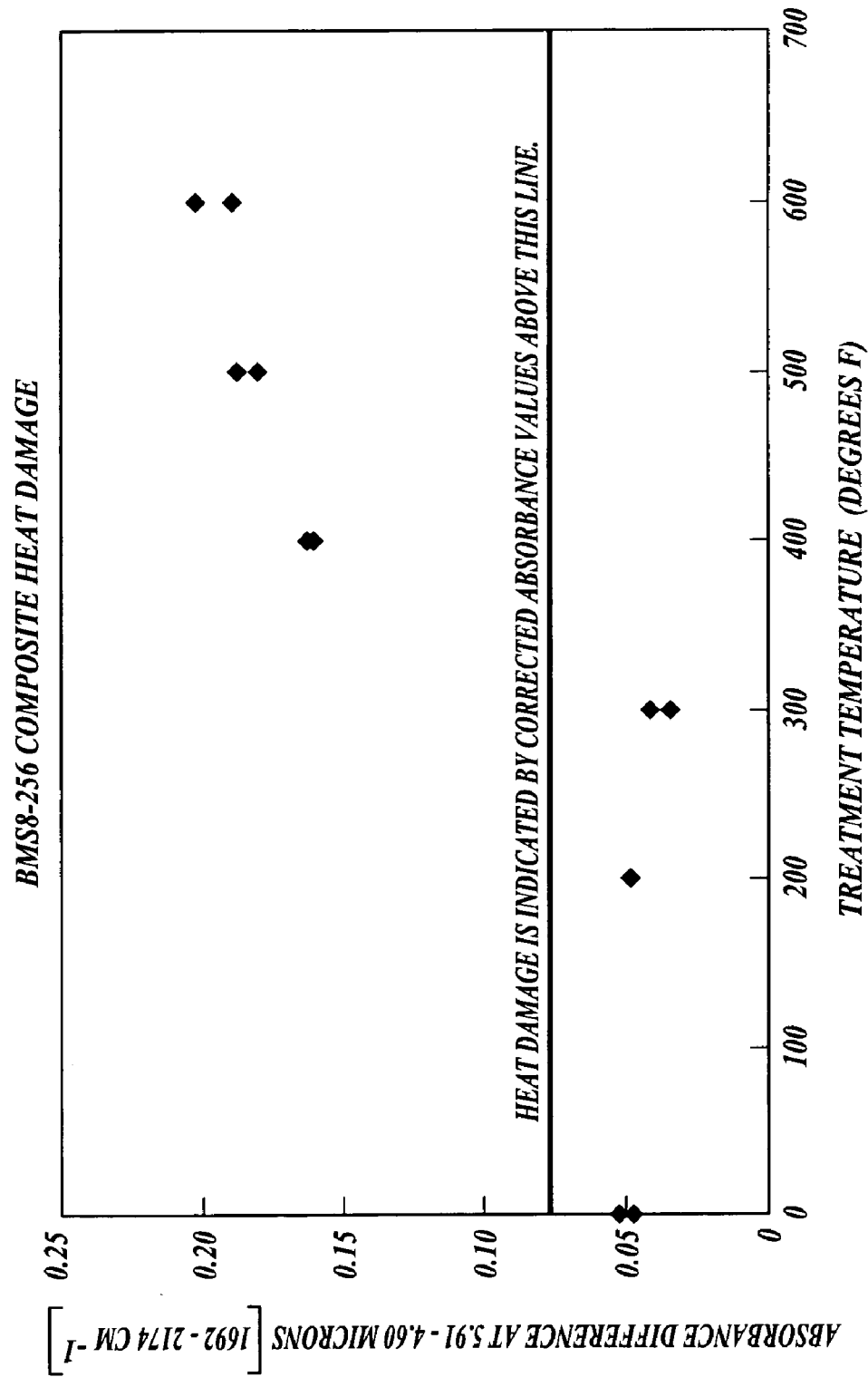
FIG. 11 is a graph of absorbance difference for a second exemplary resin-fiber composite exposed to heat.

By way of example but not limitation, FIG. 11 shows heat damage to the exemplary composite BMS 8-256 indicated by absorbance differences. Absorbance at 2174 cm-1 is subtracted from absorbance at 1692 cm-1. According to this exemplary embodiment, heat damage is indicated by absorbance difference greater than around 0.075. Absorbance for temperature exposures of 400 degrees and greater for 1 hour exceed 0.15, while those for 300 degrees or less are approximately 0.5.

The absorbance differences graphed on FIG. 11 are those of Table D below:

TABLE D

| Temperature | ABS @ 5.91 microns – ABS @ 4.60 microns |
|---|---|
| 0 | 0.052 |
| 0 | 0.047 |
| 200 | 0.048 |
| 200 | 0.048 |
| 300 | 0.034 |
| 300 | 0.041 |
| 400 | 0.163 |
| 400 | 0.161 |
| 500 | 0.181 |
| 500 | 0.188 |
| 600 | 0.19 |
| 600 | 0.203 |

In an alternate embodiment, corrected absorbance at 4.60 μm or approximately 2174 wavenumbers may be utilized to indicate heat exposure. Absorbance in this example may be equalized by subtracting a reference absorbance at 5 μm or 2000 wavenumbers. Absorbance values less than 0.015 or negative indicate heat damage of 400 degree exposure or greater for 1 hour.

Figure 12:
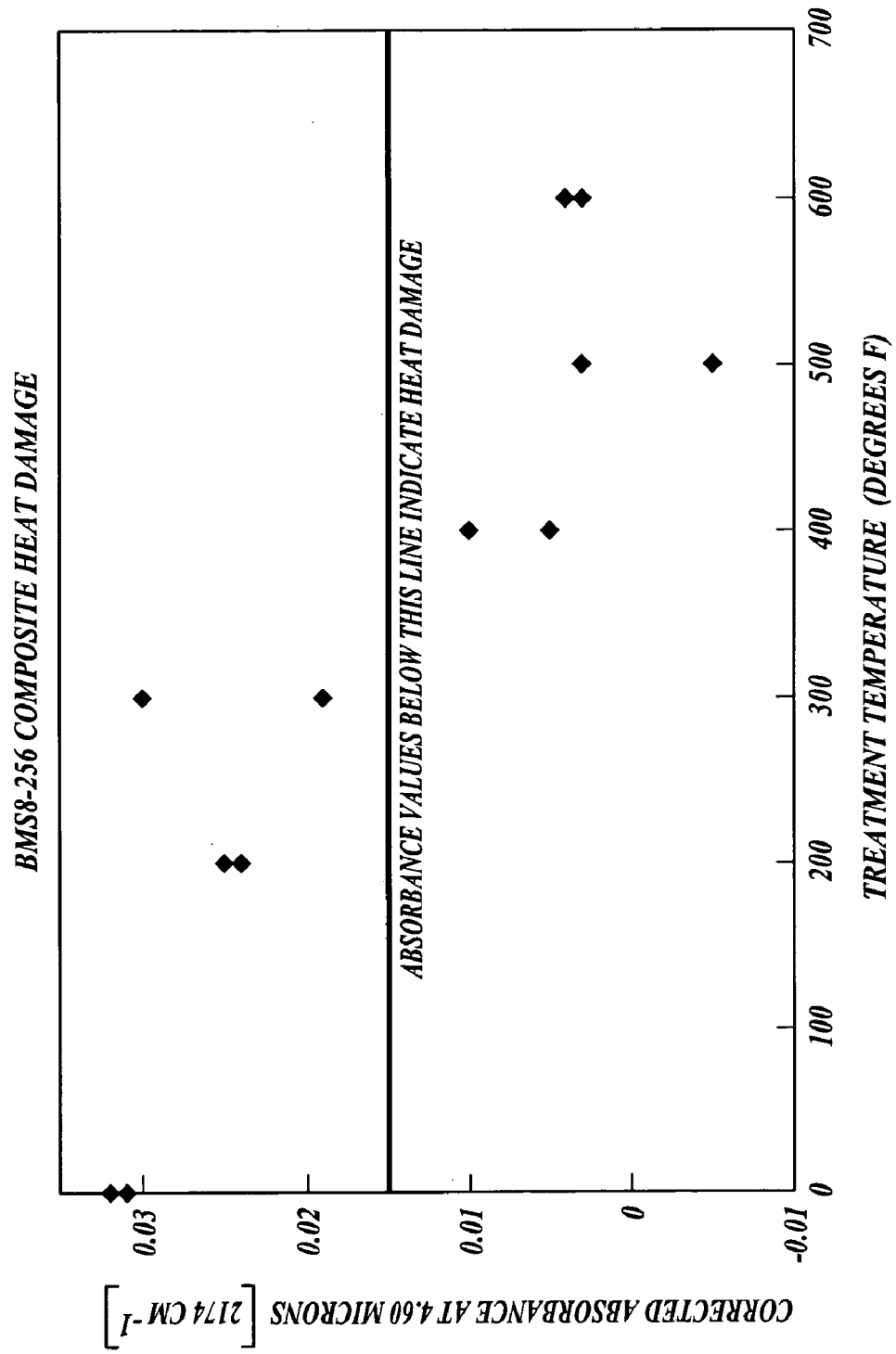
FIG. 12 is a graph of corrected absorbance for a second exemplary resin-fiber composite exposed to heat.

FIG. 12 is a graph of the data of Table E below:

TABLE E

| Temperature | Corrected absorbance at 4.60 microns (subtract ref. ABS at 5.00 microns) |
|---|---|
| 0 | 0.032 |
| 0 | 0.031 |
| 200 | 0.024 |
| 200 | 0.025 |
| 300 | 0.019 |
| 300 | 0.03 |
| 400 | 0.01 |
| 400 | 0.005 |
| 500 | −0.005 |
| 500 | 0.003 |
| 600 | 0.003 |
| 600 | 0.004 |

Figure 13:
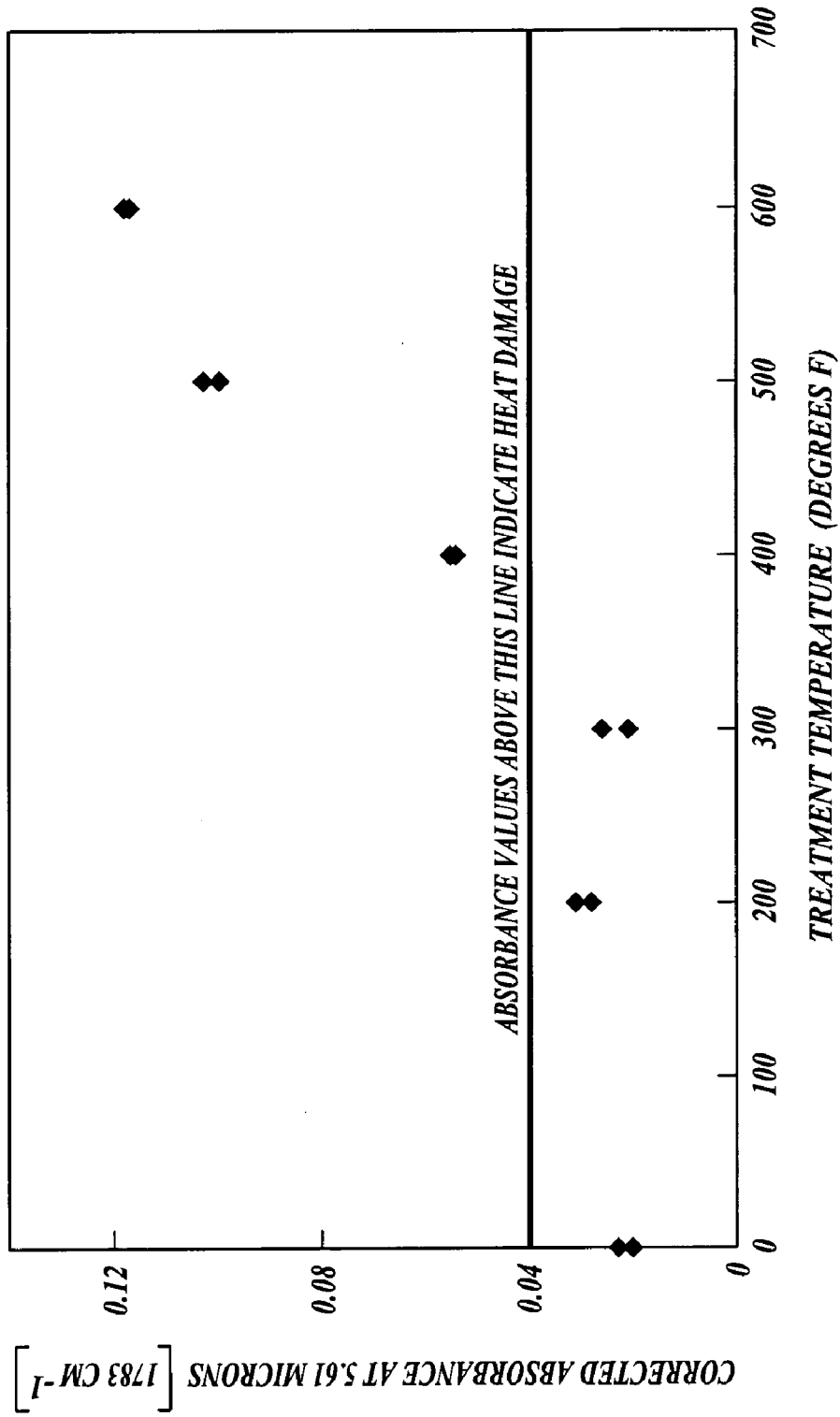
FIG. 13 is a graph of corrected absorbance for a second exemplary resin-fiber composite exposed to heat.

FIG. 13 shows a further exemplary embodiment of the present invention as applied to BMS 8-256. FIG. 13 is a graph of corrected absorbance values at 5.61 μm or 1783 wavenumbers over a range of temperature exposures. At temperature exposures of 400 degrees and greater, absorbance values above 0.04 indicate such exposure, while absorbance values for exposures of 300 degrees F. or less are typically between 0.02 and 0.04.

The data graphed in FIG. 13 are that shown in Table F below:

TABLE F

| Temperature | Corrected absorbance at 5.61 microns (subtract ref. ABS at 5.00 microns) |
|---|---|
| 0 | 0.032 |
| 0 | 0.03 |
| 200 | 0.028 |
| 200 | 0.031 |
| 300 | 0.021 |
| 300 | 0.026 |
| 400 | 0.054 |
| 400 | 0.055 |
| 500 | 0.1 |
| 500 | 0.103 |
| 600 | 0.117 |
| 600 | 0.118 |

Figure 14:
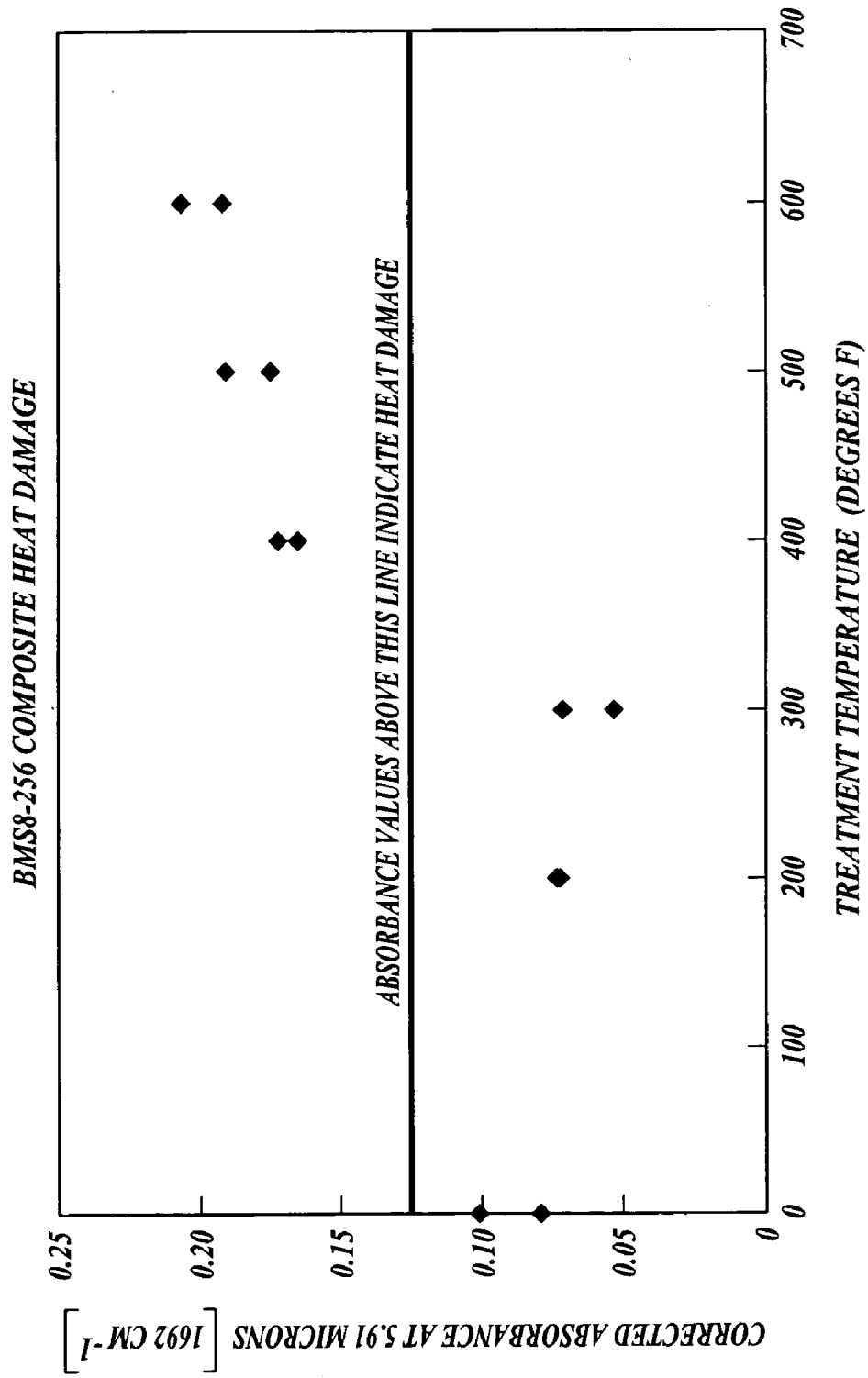
FIG. 14 is a graph of corrected absorbance for a second exemplary resin-fiber composite exposed to heat.

In FIG. 14, in a further exemplary embodiment, absorbance heat damage or a degree of heat exposure for the exemplary composite BMS 8-256 may be correlated to corrected absorbance at 5.91 μm or 1692 wavenumbers. Heat exposure of 400 degrees F. or greater is indicated by an absorbance value greater than 0.125, while exposures of 300 degrees or less are typically between 0.05 and 0.1. Absorbance is again corrected by subtracting absorbance at 5 μm or 2000 cm-1. Exposures to 400 degrees F. or greater demonstrate absorbance at 0.15 or higher.

The data graphed in FIG. 14 are that of Table G below:

TABLE G

| Temperature | Corrected absorbance at 5.91 microns (subtract ref. ABS at 5.00 microns) |
|---|---|
| 0 | 0.079 |
| 0 | 0.101 |
| 200 | 0.072 |
| 200 | 0.073 |
| 300 | 0.053 |
| 300 | 0.071 |
| 400 | 0.054 |
| 400 | 0.166 |
| 500 | 0.176 |
| 500 | 0.191 |
| 600 | 0.192 |
| 600 | 0.207 |

Figure 15:
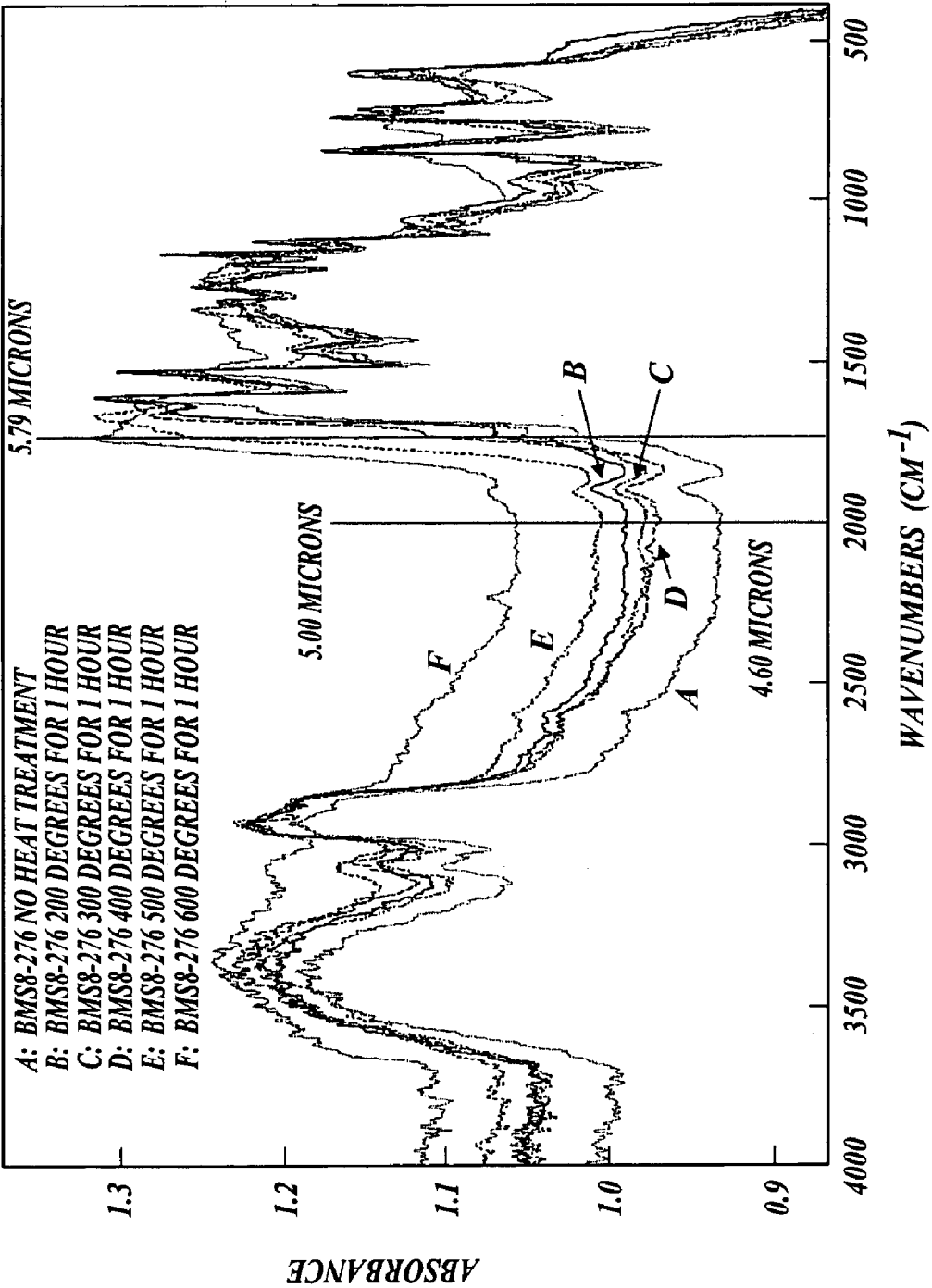
FIG. 15 is a graph of infrared absorbance of a third exemplary resin-fiber composite.
Figure 16:
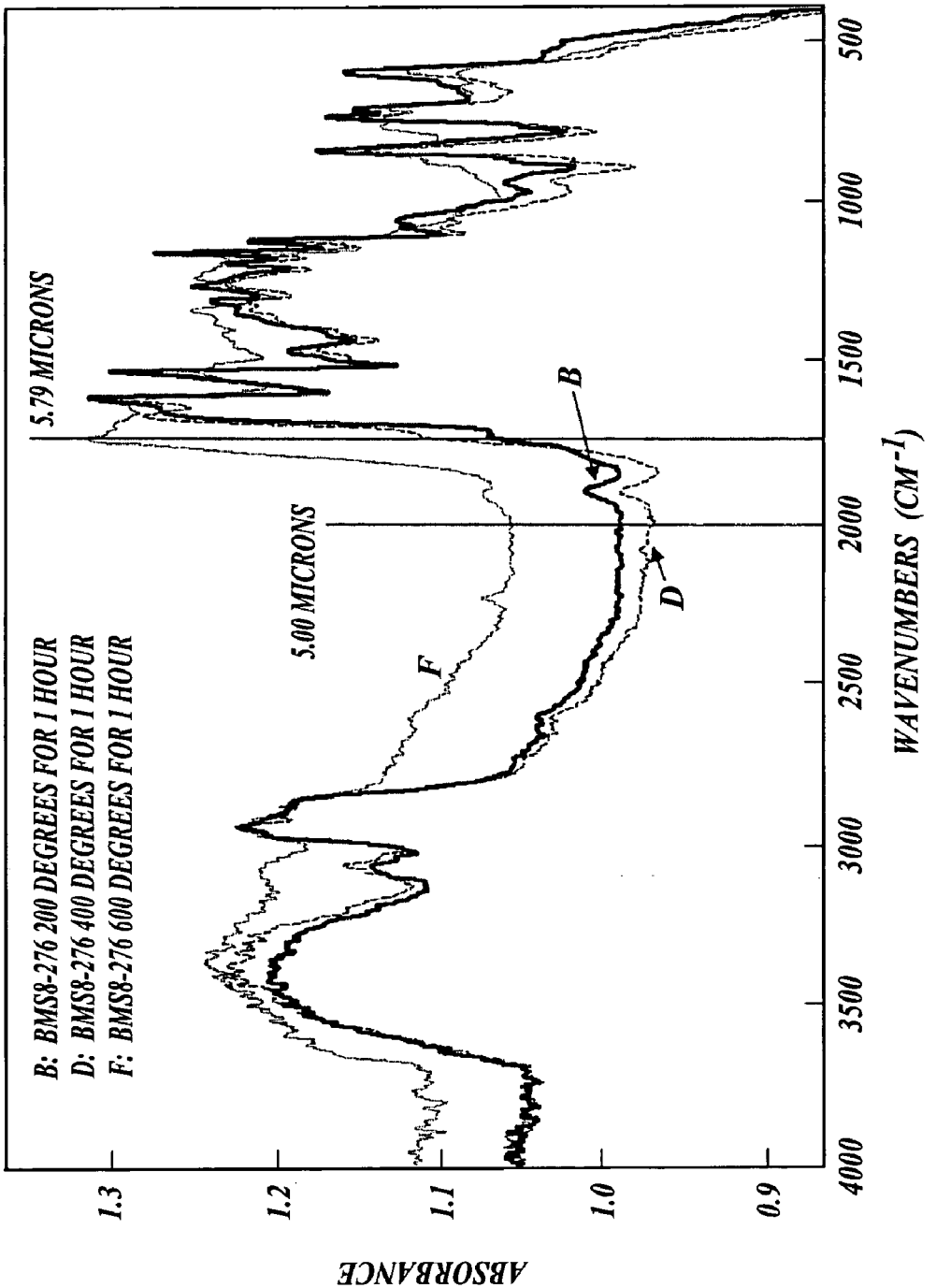
FIG. 16 is a graph of infrared absorbance of a third exemplary resin-fiber composite exposed to heat.
Figure 17:
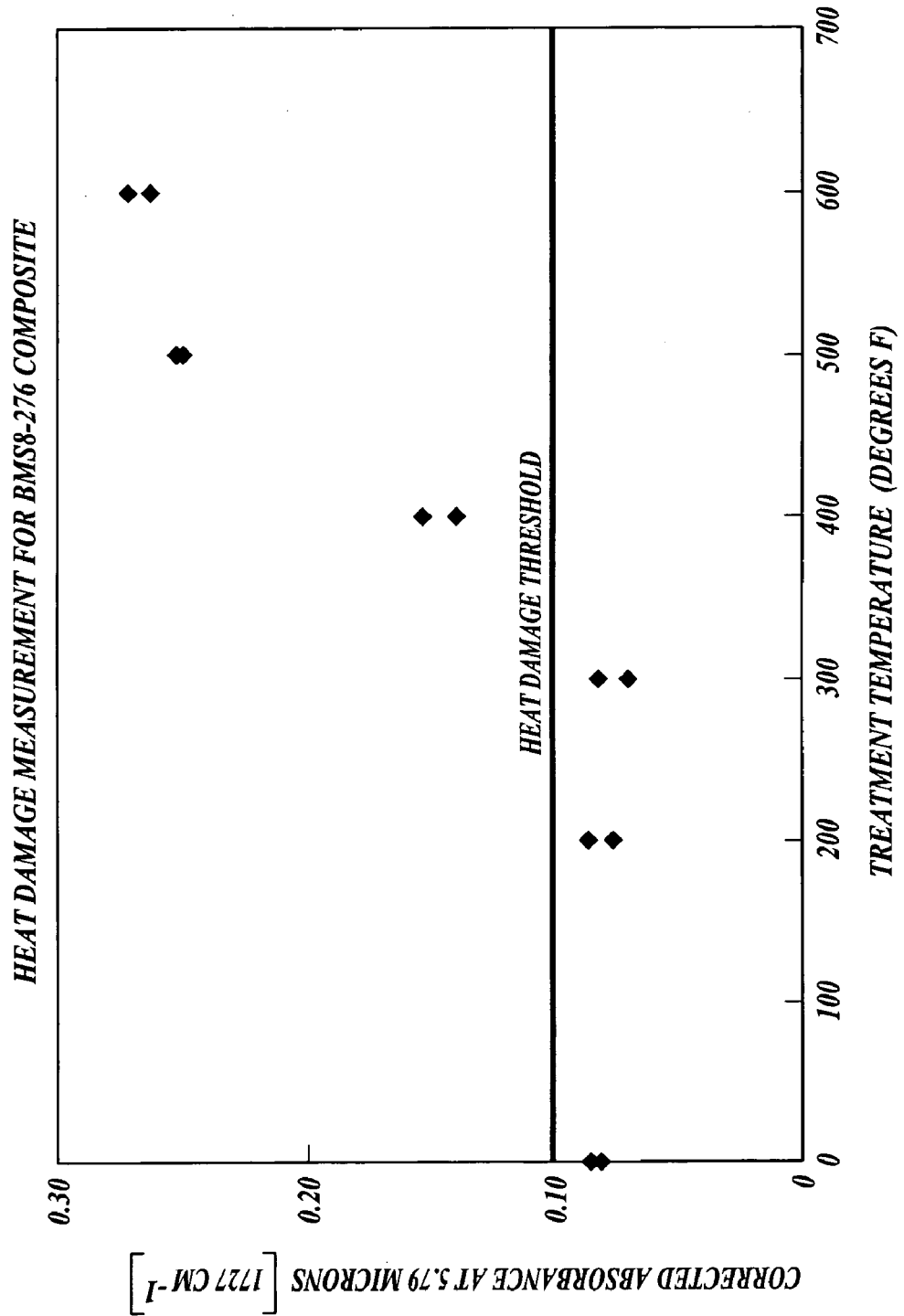
FIG. 17 is a graph of corrected absorbance for a third exemplary resin-fiber composite.

FIGS. 15 and 16 show spectra for heat exposed samples for a third exemplary resin-fiber composite designated BMS 8-276. FIG. 17 is a plot of a resulting correlation of heat exposure to absorbance.

FIG. 15 is a graph of six infrared absorbance spectra over a range of wavenumbers from 4000 wavenumbers to approximately 400 wavenumbers, with no heat exposure for spectrum A, 200 degree heat exposure for 1 hour for spectrum B, 300 degrees for 1 hour for spectrum C, 400 degrees for 1 hour for spectrum D, 500 degrees for 1 hour for spectrum E, and 600 degrees for spectrum F. The spectra for BMS 8-276 typically show less variation at the middle heat ranges of 300 and 400 degrees than BMS 8-212 and BMS 8-276. FIG. 16 shows absorbances for three of the six spectra from FIG. 15. Spectrum B reflects 200 degree heat exposure, spectrum D reflects 400 degree heat exposure, and spectrum F reflects 600 degree heat exposure. Reference lines at 5.0 μm or 2000 wavenumbers and 5.79 μm or 1727 wavenumbers are drawn for reference. By way of example but not limitation, variation at these two wavenumbers permits correlation of heat exposure to absorbance.

FIG. 17 is a graph of corrected absorbance at 5.79 μm or 1727 wavenumbers of BMS 8-276 resulting from heat exposure. The corrected absorbance is suitably obtained by subtracting absorbance at a reference wavelength of 5 μm or 2000 wavenumbers from absorbance at 5.79 μm or 1727 wavenumbers. A heat damage threshold of exposure of 400 degrees at 1 hour is indicated in FIG. 17 by corrected absorbances of greater than around 0.1. Heat exposures of 400 degrees F or greater are reflected by corrected absorbances of approximately 0.14 and higher, while 300 degree and less heat exposure is typically approximately 0.075. The absorbance charted on FIG. 17 is that of Table H below reflecting increasing absorbance with increasing temperature.

TABLE H

| Temperature | ABS @ 5.79 microns − ABS @ 5 microns |
|---|---|
| 0 | 0.081 |
| 0 | 0.085 |
| 200 | 0.086 |
| 200 | 0.076 |
| 300 | 0.07 |
| 300 | 0.082 |
| 400 | 0.14 |
| 400 | 0.154 |
| 500 | 0.253 |
| 500 | 0.25 |
| 600 | 0.263 |
| 600 | 0.272 |

Figure 18:
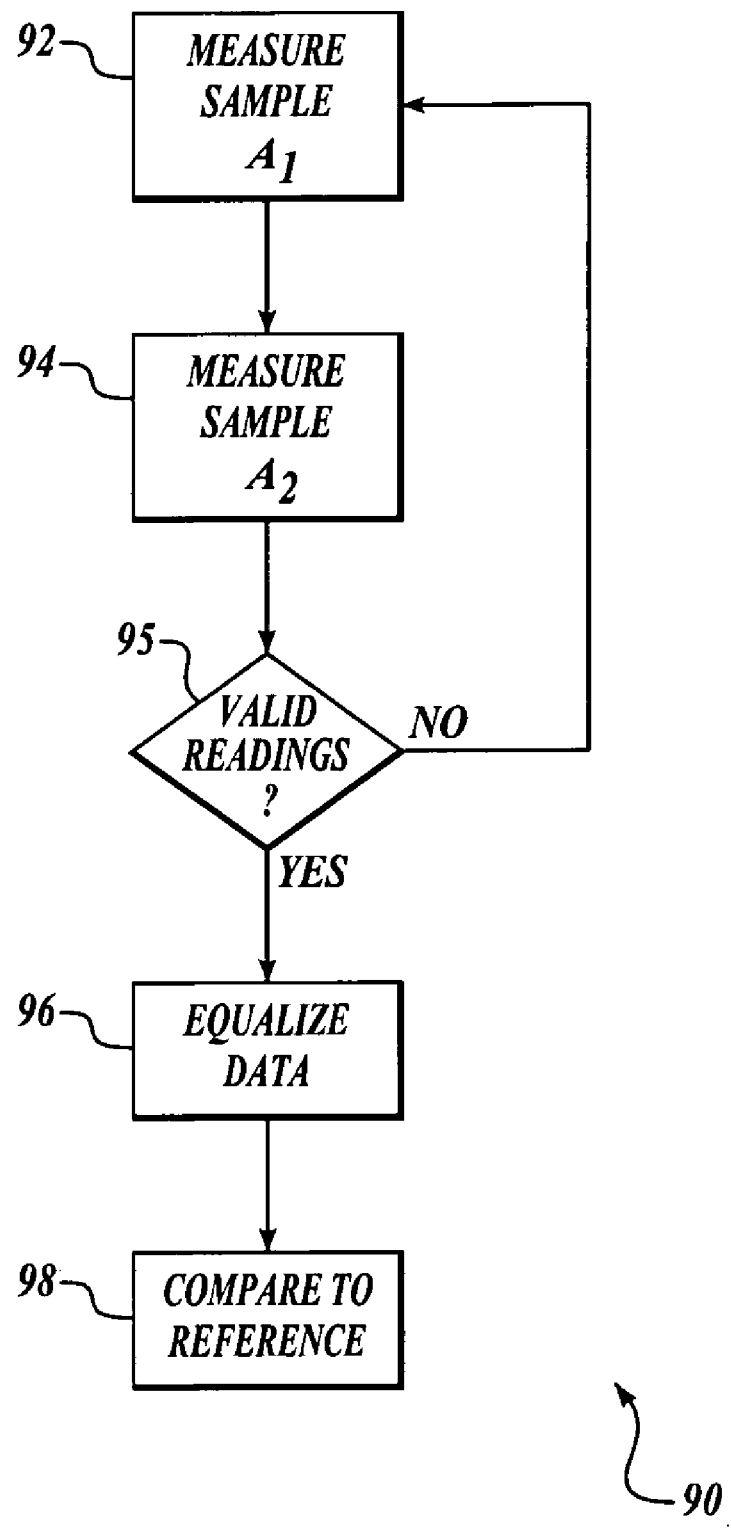
FIG. 18 is a flow chart of an exemplary testing method of the present invention.

Referring now to FIG. 18, an exemplary routine 90 of the present invention is illustrated in flow chart form. At a block 92 the infrared absorbance $A_1$ of the sample at a first wavelength is measured. At a block 94 the infrared absorbance $A_2$ of a sample at a second wavelength is measured.

At a decision block 95 the sample measurements are reviewed for validity. For example, with attenuated total reflectance, if absorbance of certain frequencies does not reach a certain minimum level, then insufficient pressure may have been applied to the testing device holding it against the sample. Alternately, spurious measurements may be indicative of contamination or remaining coatings. If the readings are not within feasible ranges, then new readings are taken by returning to block 92. Otherwise, with valid data the routine 90 continues at a block 96 where the data may be equalized. Equalization of the data, as described above, suitably may include subtraction of more variable or active readings at alternated frequencies, or subtraction by absorbance or readings at more stable reference frequencies.

The equalized data including $A_1$ and $A_1$ may then be compared to a reference at a block 98 to determine a degree or amount of heat exposure of the sample or substrate, such as by comparing the equalized data to graphs or tables of the reference sample at exposures to specific degrees or amounts of heat.

Figure 19:
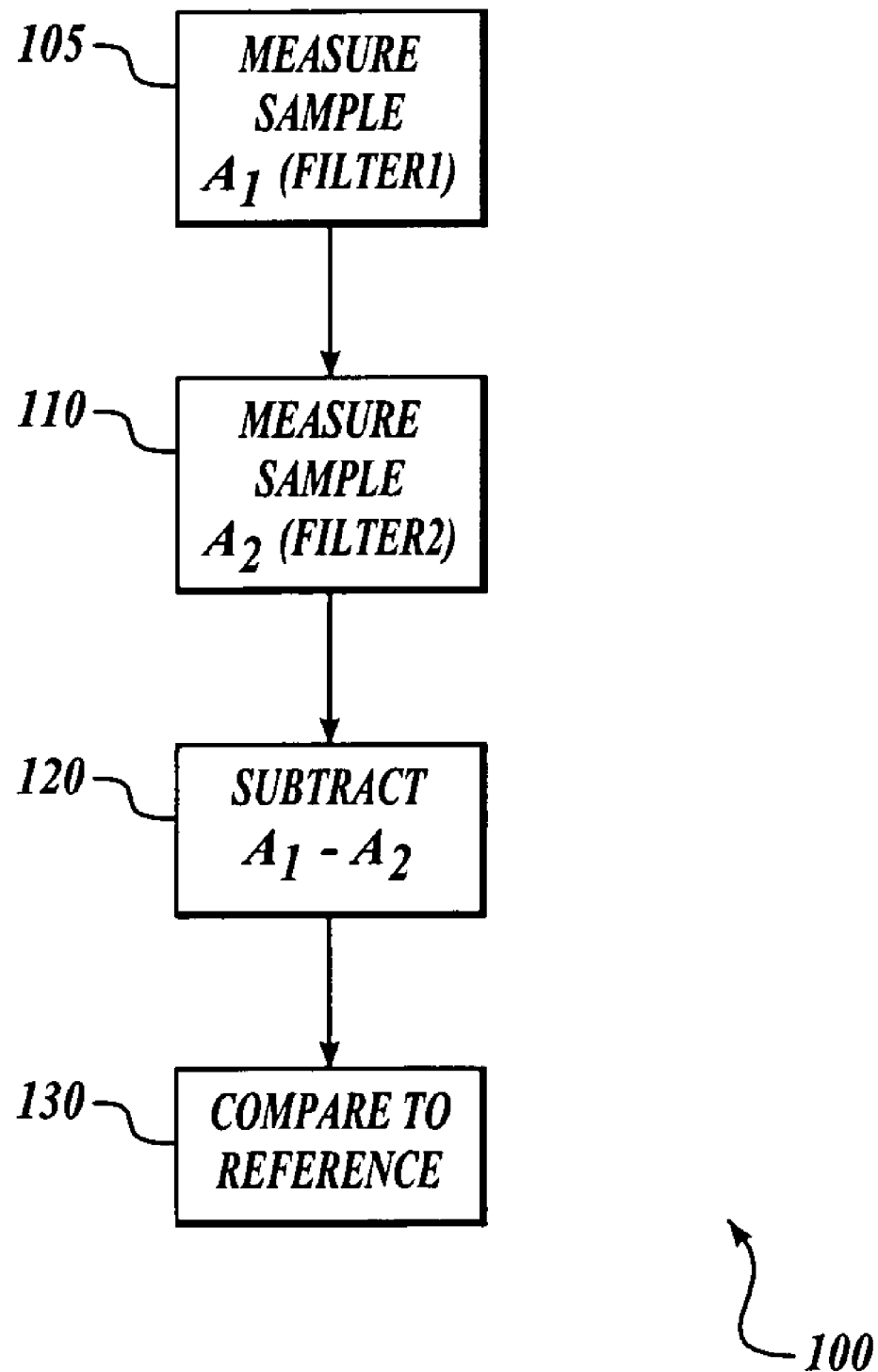
FIG. 19 is a flow chart of a further exemplary testing method of the present invention.

Turning to FIG. 19, an alternate routine 100 of the present invention is shown in flow chart form. At a block 105, absorbance $A_1$ at a first wavelength is measured utilizing a first filter. At a block 110, the infrared absorbance $A_2$ of the sample at a second wavelength is measured utilizing a second filter. At a block 120 $A_2$ is subtracted from $A_1$ to form a difference. At a block 130, the resulting difference is compared to a reference to determine a degree of heat exposure of the sample.

It will also be appreciated that, for some resin-fiber composites, heat exposure may directly correlate with absorbance at a single frequency without utilization of alternate absorbances.

Figure 20:
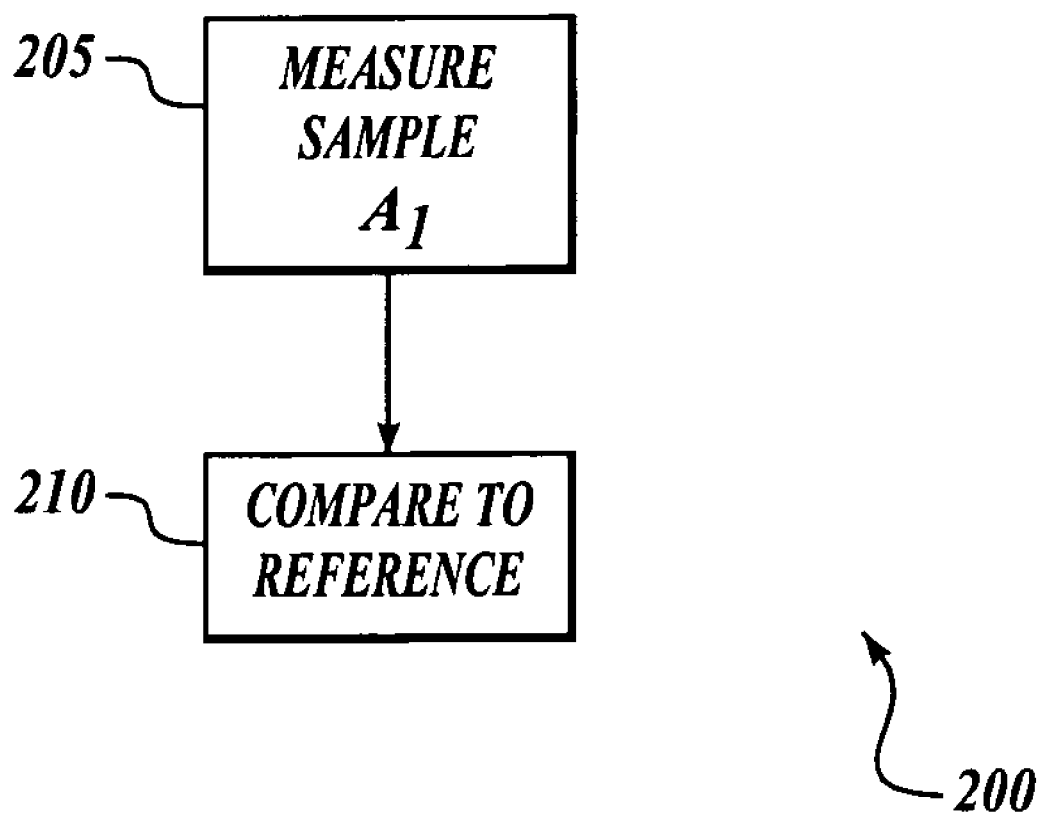
FIG. 20 is a flow chart of a third exemplary testing method of the present invention.

FIG. 20 shows a flow chart of an exemplary method 200 of the present embodiment utilizing absorbance at a single wavelength. At a block 205, infrared absorbance of the sample $A_1$ is measured. At a block 210, that absorbance is compared to a reference to determine a degree or amount of heat exposure of the sample or substrate.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A non-destructive method for determining an amount of heat exposure to a resin-fiber composite substrate, the method comprising:
    non-destructively determining a value $I_s$ of infrared energy reflected by a surface on the composite substrate; and
    correlating the value $I_s$ of the infrared energy reflected to an amount of heat exposure, wherein determining $I_s$ includes determining absorbance at at least one wavenumber wherein increased infrared absorbance reflects exposure by the composite substrate to heat greater than 300 degrees F.

2. The method of claim 1, further comprising determining a value $I_r$ of infrared energy reflected from a reference composite surface.

3. The method of claim 2, further comprising comparing $I_s$ with $I_r$.

4. The method of claim 1, wherein determining the infrared absorbance includes using an infrared spectrometer.

5. The method of claim 1, wherein determining the infrared absorbance includes using at least one of an infrared filter spectrometer and an ellipsoidal mirror collector.

6. The method of claim 1, wherein determining the infrared absorbance includes using an attenuated total reflectance collector.

7. The method of claim 1, wherein determining the infrared absorbance includes using an infrared spectrometer having at least two filters.

8. The method of claim 7, wherein the at least two filters include narrow bandpass infrared filters.

9. The method of claim 1, wherein the at least one wavenumber is around 2174 cm−1.

10. The method of claim 1, wherein the at least one wavenumber is around 1783 cm−1.

11. The method of claim 1, wherein the at least one wavenumber is around 1727 cm−1.

12. The method of claim 1, wherein the at least one wavenumber is around 1767 cm−1.

13. The method of claim 1, wherein the at least one wavenumber is around 1692 cm−1.

14. The method of claim 1, wherein the at least one wavenumber is around 1678 cm−1.

15. The method of claim 1, wherein the at least one wavenumber is around 1522 cm−1.

16. The method of claim 1, wherein correlating the infrared absorbance to an amount of heat exposure of the sample includes determining a difference between infrared absorbance of the composite substrate at at least two wavenumbers, wherein absorbance at a second wavenumber is subtracted from absorbance from a first wavenumber, and a difference greater than a threshold amount reflects exposure of the composite substrate to heat greater than 300 degrees F.

17. The method of claim 16, wherein the second wavenumber is around 2000 cm−1.

18. The method of claim 16, wherein the first wavenumber is around 1522 cm−1 and the second wavenumber is around 1678 cm−1 and the threshold amount is approximately 0.07.

19. The method of claim 16, wherein the first wavenumber is around 1629 cm−1 and the second wavenumber is around 2174 cm−1 and the threshold amount is greater than 0.15.

20. A non-destructive method for determining an amount of heat damage to a resin-fiber composite sample, the method comprising:
    transmitting an infrared beam onto a sample of a resin-fiber composite, wherein transmitting an infrared beam includes transmitting the infrared beam in a direction approximately in alignment with fibers in the sample:
    detecting a reflected infrared beam reflected by the sample;
    determining infrared absorbance of the sample; and
    correlating the infrared absorbance to an amount of heat damage to the sample, wherein correlating the infrared absorbance includes determining absorbance at at least one wavenumber wherein increased absorbance reflects exposure by the composite sample to heat greater than 300 degrees F.

21. The method of claim 20, wherein determining the infrared absorbance includes using an infrared spectrometer.

22. The method of claim 20, wherein the at least one wavenumber is around 2174 cm−1.

23. The method of claim 20, wherein the at least one wavenumber is around 1783 cm−1.

24. The method of claim 20, wherein the at least one wavenumber is around 1727 cm−1.

25. The method of claim 20, wherein the at least one wavenumber is around 1767 cm−1.

26. The method of claim 20, wherein the at least one wavenumber is around 1692 cm−1.

27. The method of claim 20, wherein the at least one wavenumber is around 1678 cm−1.

28. The method of claim 20, wherein the at least one wavenumber is around 1522 cm−1.

29. The method of claim 20, wherein correlating the infrared absorbance to an amount of heat damage of the sample includes deriving a difference between infrared absorbance at at least two wave numbers wherein absorbance at a second wavenumber is subtracted from absorbance from a first wavenumber, and a difference greater than a threshold amount reflects exposure by the composite substrate to heat greater than 300 degrees F.

30. The method of claim 29, wherein deriving a difference between infrared absorbance of the sample at at least two wavenumbers includes deriving a difference between infrared absorbance at a first wavenumber of around 1522 cm−1 and at a second wavenumber of around 1678 cm−1.

31. The method of claim 29, wherein deriving a difference between infrared absorbance of the sample at at least two wavenumbers includes deriving a difference between infrared absorbance at a first wavenumber of around 1692 cm−1 and at a second wavenumber of around 2174 cm−1.

32. The method of claim 20, wherein detecting a reflected infrared beam reflected by the sample includes filtering the reflected infrared beam.

33. The method of claim 32, wherein filtering the reflected infrared beam includes utilizing at least two filters.

34. A non-destructive method for determining an amount of heat exposure of a resin-fiber composite sample, the method comprising:
    transmitting an infrared beam onto a sample of resin-fiber composite;
    detecting a reflected infrared beam reflected by the sample;
    determining a first infrared absorbance of the sample from the reflected infrared beam at a first wavenumber, wherein the first wavenumber corresponds with an infrared spectra of a heat damaged composite surface;
    determining a second infrared absorbance of the sample from the reflected infrared beam at a second wavenumber, and the second wavenumber corresponds with an infrared spectra of a heat damaged composite surface;
    deriving a first difference between the first infrared absorbance and the second infrared absorbance; and
    quantitatively determining an amount of heat exposure by correlating the first difference to a plurality of reference samples exposed to various amounts of heat.

35. The method of claim 34, wherein determining at least one of the first infrared absorbance and the second infrared absorbance includes using an infrared filter spectrometer.

36. The method of claim 34, wherein the first wavenumber is around 1678 cm−1, the second wavenumber is around 2000 cm−1, and the first difference is greater than approximately 0.07.

37. The method of claim 34, wherein the first wavenumber is around 1767 cm−1, the second wavenumber is around 2000 cm−1, and the first difference is greater than approximately 0.04.

38. The method of claim 34, wherein the first wavenumber is around 2174 cm−1, the second wavenumber is around 2000 cm−1, and the first difference is greater than approximately 0.04.

39. The method of claim 34, wherein the first wavenumber is around 1783 cm−1, the second wavenumber is around 2000 cm−1, and the first difference is greater than approximately 0.04.

40. The method of claim 34, wherein the first wavenumber is around 1727 cm−1, the second wavenumber is around 2000 cm−1, and the first difference is greater than approximately 0.075.

41. The method of claim 34, wherein the first wavenumber is around 1522 cm−1, the second wavenumber is around 1678 cm−1, and the first difference is less than approximately 0.2.

42. The method of claim 34, wherein the first wavenumber is around 1692 cm−1, the second wavenumber is around 2174 cm−1, and the first difference is less than approximately 0.15.

43. A non-destructive method for determining a degree of heat exposure of a resin-fiber composite substrate, the method comprising:
    determining an alignment direction of fibers in the substrate;
    transmitting an infrared beam onto the substrate in alignment with the alignment direction;
    filtering with a first filter a reflected infrared beam reflected by the substrate;
    detecting a first filtered portion of the reflected infrared beam;
    determining a first infrared absorbance of the substrate; and correlating the first infrared absorbance to a degree of heat exposure by comparison to a plurality of reference samples exposed to various amounts of heat, including at least one reference sample exposed to temperatures over 300 degrees F.

44. The method of claim 43 wherein determining a first infrared absorbance includes determining absorbance at a wavenumber of around 2174 cm−1.

45. The method of claim 43 wherein determining a first infrared absorbance includes determining absorbance at a wavenumber of around 2000 cm−1.

46. The method of claim 43 wherein determining a first infrared absorbance includes determining absorbance at a wavenumber of around 1783 cm−1.

47. The method of claim 43 wherein determining a first infrared absorbance includes detennining absorbance at a wavenumber of around 1727 cm−1.

48. The method of claim 43 wherein determining a first infrared absorbance includes determining absorbance at a wavenumber of around 1767 cm−1.

49. The method of claim 43 wherein determining a first infrared absorbance includes determining abs orbance at a wavenumber of around 1692 cm−1.

50. The method of claim 43 wherein determining a first infrared absorbance includes determining absorbance at a wavenumber of around 1678 cm−1.

51. The method of claim 43 wherein determining a first infrared absorbance includes determining abs orbance at a wavenumber of around 1522 cm−1.

52. The method of claim 43, further comprising:

filtering with a second filter a reflected infrared beam reflected by the substrate;

detecting a second filtered portion of the reflected infrared beam; and determining a second infrared absorbance of the substrate.

53. The method of claim 52, further comprising subtracting the second infrared absorbance from the first infrared absorbance.

54. The method of claim 52 wherein determining a first infrared absorbance includes determining absorbance at a wavenumber of around 1522 cm−1, and determining a second infrared absorbance includes determining absorbance at a wavenumber of around 1678 cm−1.

55. The method of claim 52 wherein determining a first infrared absorbance includes determining absorbance at a wavenumber of around 1692 cm−1, and determining a second infrared absorbance includes determining absorbance at a wavenumber of around 2174 cm−1.

* * * * *